US012745741B2

(12) United States Patent
Suzuki et al.

(10) Patent No.: US 12,745,741 B2
(45) Date of Patent: Sep. 29, 2026

(54) REDUCING NITRATE REDUCTASE ACTIVITY IN TABACCO AND METHODS FOR ITS USE

(71) Applicant: Japan Tobacco Inc., Tokyo (JP)

(72) Inventors: Shoichi Suzuki, Tokyo (JP); Ryo Okada, Tokyo (JP); Soichiro Noguchi, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 84 days.

(21) Appl. No.: 18/331,646

(22) Filed: Jun. 8, 2023

(65) Prior Publication Data

US 2023/0320309 A1 Oct. 12, 2023

Related U.S. Application Data

(63) Continuation of application No. PCT/JP2021/045295, filed on Dec. 9, 2021.

(30) Foreign Application Priority Data

Dec. 9, 2020 (JP) ................................ 2020-203916

(51) Int. Cl.
*A01H 5/12* (2018.01)
*A01H 1/00* (2006.01)
*A01H 6/82* (2018.01)

(52) U.S. Cl.
CPC ............. *A01H 6/823* (2018.05); *A01H 1/101* (2021.01); *A01H 5/12* (2013.01); *C12Y 107/01001* (2013.01)

(58) Field of Classification Search
CPC .......... A01H 6/823; A01H 5/12; A01H 1/101; C12N 9/0044; C12N 15/8243; C12Y 107/01001; A24B 13/00
See application file for complete search history.

(56) References Cited

FOREIGN PATENT DOCUMENTS

| | | | | |
|---|---|---|---|---|
| WO | WO 2015/197727 A2 | 12/2015 | | |
| WO | WO 2016/046288 A1 | 3/2016 | | |
| WO | WO-2020141062 A1 * | 7/2020 | | A01H 1/06 |

OTHER PUBLICATIONS

Bachmann, Markus et al., (Identification of Ser-543 as the major regulatory phosphorylation site in spinach leaf nitrate reductase. The Plant cell vol. 8,3 (1996): 505-17 (Year: 1996).*
Extended European Search Report for European Application No. 21903460.0, dated Oct. 17, 2024.
Lu et al., "Expression of a constitutively active nitrate reductase variant in tobacco reduces tobacco-specific nitrosamine accumulation in cured leaves and cigarette smoke," Plant Biotechnology Journal, vol. 14, 2016, pp. 1500-1510.
Bachmann et al., "Identification of Ser-543 as the Major Regulatory Phosphorylation Site in Spinach Leaf Nitrate Reductase," The Plant Cell, vol. 8, 1996, pp. 505-517.
Lea et al., "Mutation of the regulatory phosphorylation site of tobacco nitrate reductase results in high nitrite excretion and No emission from leaf and root tissue," Planta, vol. 219, 2004, pp. 59-65.
Lea et al., "Posttranslational Regulation of Nitrate Reductase Strongly Affects the Levels of Free Amino Acids and Nitrate, whereas Transcriptional Regulation Has Only Minor Influence," Plant Physiology, vol. 140, 2006, pp. 1085-1094.
Lillo et al., "Mutation of the regulatory phosphorylation site of tobacco nitrate reductase results in constitutive activation of the enzyme in vivo and nitrite accumulation," The Plant Journal, vol. 35, 2003, pp. 566-573.
Tajima et al., "Construction of Mutant Panel in *Nicotiana tabacum* L. tobacco," Heisei 23-nen Nihonshokubutsubyorigakkal Taikai P258, Abstract 226, 2011, 115 pages total, with English abstract.
Japanese Office Action for Japanese Application No. 2022-568325, dated Dec. 24, 2024, with English translation.

* cited by examiner

*Primary Examiner* — Amjad Abraham
*Assistant Examiner* — Christian Jose Ordaz
(74) *Attorney, Agent, or Firm* — Birch, Stewart, Kolasch & Birch, LLP

(57) ABSTRACT

The present invention relates to a tobacco plant and the like. The tobacco plant of the present invention contains nitrate reductase in which an amino acid residue corresponding to position 525 in an amino acid sequence corresponding to SEQ ID NO: 2 or 4 is mutated from proline to an amino acid residue other than proline. In one embodiment, the tobacco plant has one or more properties of the following (a) to (c): (a) the activity of the nitrate reductase under the dark condition is 80% or more of the activity of the nitrate reductase under the light condition; (b) an individual is essentially equivalent to a control in growth; and/or (c) nitric acid decreases as compared with the control, wherein the control is a tobacco plant containing nitrate reductase consisting of the amino acid sequence of SEQ ID NO: 2 or 4.

12 Claims, 17 Drawing Sheets

Specification includes a Sequence Listing.

Plant bodies around 3 W after transplantation

S523D-16 and 20, which are two lines, and non-expressing null line at T1 generation
WT-13 and 22, which are two lines, and non-expressing null line at T1 generation Initial vegetation of S523D recombinant (T2 generation)
(11 days after temporary planting)

S523D-Null S523D-16 n=4 n=4 error bar: SE

Fig.7-6 M2 generation n=4 (P525S), n=3 (S537L) * (P<0.05)

Fig.7-7 M2 generation n=4 (P525L), n=3(G485E, G483K) * (P<0.05)

n=4 n=3 (P525_Homo: n=2)

n=4

** (P<0.01)

n=4

* (P<0.05)

NIA1_P525L (M3)
Mutated Homo WT

NIA1_P525S (M3)
Mutated Homo WT

NIA1_P525L (M3)
Mutated Homo Mutated Hetero WT

NIA1_P525S (M3)
Mutated Homo Mutated Hetero WT

N=4, **P<0.01

N=4, **P<0.01

N=4, **P<0.01

N=9(S523D-OE, Null), 6(P525S, P525L), **P<0.01

N=9(S523D-OE, Null), 6(P525S, P525L), **P<0.01

N=9(S523D-OE, Null), 6(P525S, P525L), **P<0.01

Anthesis

S523D-OE S523D-null 13 days before anthesis 6 days after anthesis n=20 (only P525L Homo: 19)

*P<0.05、**P<0.01 error bar: SD

REDUCING NITRATE REDUCTASE ACTIVITY IN TABACCO AND METHODS FOR ITS USE

CROSS REFERENCE TO RELATED APPLICATIONS

This application is a Continuation of PCT International Application No. PCT/JP2021/045295, filed on Dec. 9, 2021, which claims priority under 35 U.S.C. 119(a) to Patent Application No. 2020-203916, filed in Japan on Dec. 9, 2020, all of which are hereby expressly incorporated by reference into the present application.

REFERENCE TO ELECTRONIC SEQUENCE LISTING

The application contains a Sequence Listing which has been submitted electronically in .XML format and is hereby incorporated by reference in its entirety. Said .XML copy, created on Jun. 6, 2023, is named "FA0092-21321US-01 Sequence Listing.xml" and is 45,311 bytes in size. The sequence listing contained in this .XML file is part of the specification and is hereby incorporated by reference herein in its entirety.

TECHNICAL FIELD

The present invention relates to a tobacco plant, a method for producing the same, a tobacco product, and the like.

BACKGROUND ART

Tobacco-specific nitrosamines (TSNAs) are nitrosated products of tobacco alkaloids generated mainly at the time of curing tobacco leaves. Tobacco plants accumulate high-level free nitrates in leaves, and this relates to the generation of TSNAs. Substances participating directly in TSNA generation at the time of curing tobacco leaves are recognized to be nitrites. Although the free nitrates accumulated in the leaves of tobacco plants are converted into nitrites by nitrate reductase (NR) that tobacco has, nitrites have cytotoxicity, and are promptly metabolized. Therefore, the amount of endogenous nitrites contained in plant tissue is generally very small. It is believed that most of the nitrites participating in TSNA generation at the time of curing tobacco leaves is produced from nitrates by microorganisms inhabiting phylloplanes. That is, as leaf tissue is decomposed in a step of curing tobacco leaves, nitrates accumulated in the leaves are eluted and converted into nitrites by nitrate reductase (NR) that microorganisms inhabiting phylloplanes have.

Nitrate reductase is an enzyme that catalyzes the first step, in which nitrate nitrogen in plants is reduced to an organic form, and is regulated at transcriptional, translational, and post-translational levels. In a dark place environment, the phosphorylation and the subsequent binding to the 14-3-3 protein inactivate nitrate reductase (Lillo et al. 2004).

The Plant Cell, 8 (1996), 505-517 (NPL 1) discloses that the Ser 543 of the nitrate reductase of spinach is a phosphorylation site related to post-translational regulation using synthetic peptides and has investigated the influence of the substitution of amino acid residues there around on the affinity for NR kinase. It is shown therein that the modification of the arginine residue at the minus 3 position (R540) or the leucin at the minus 5 position (L538) from Ser 543 into alanine deteriorates the affinity for NR kinase markedly. Meanwhile, it is shown that the modification of the lysine at the minus 4 position (K539), the proline at the plus 2 position (P545), and the methionine at the plus 4 position (M547) into alanine does not have a great influence on the affinity for NR kinase. FIG. 8 of NPL 1 shows a controllable phosphorylation site highly conserved in nitrate reductases regardless of the plant species, and serine at position 523 corresponds to this in tobacco NIA2.

Plant physiology, 140(2006), 1085-1094 (NPL 2) discloses that nitrate reductase (S521D-NR) gene having the serine at position 521 of NIA2 converted into aspartic acid was introduced into the tobacco plant *Nicotiana plumbaginifolia* E23 mutant to overexpress the gene under the CaMV 35S promoter, so that, in the plant into which the S521D-NR gene is introduced (line S521D), high nitrate reductase activity was maintained constitutively day and night, and the nitric acid content of the individual was almost constant, and changed at a low level day and night. Plant J., 35(2003), 566-573 (NPL 3) shares some authors in common to NPL 2 and it describes the production of the S521D-NR construct of tobacco and tobacco into which S521D-NR is introduced.

It is clear in view of the description of NPL 1 that "S523D" is mistakenly written as "S521D" in NPLs 2 and 3.

WO 2016/046288 (PTL 1) (corresponding to Japanese Translation of PCT International Application Publication No. 2017-529850) describes a tobacco product having reduced tobacco-specific nitrosamines (TSNAs) generated from tobacco plants. It is specified that the tobacco plant contains (i) a polynucleotide containing a sequence encoding a moderated nitrate reductase enzyme, consisting of a sequence encoding a moderated nitrate reductase enzyme, or consisting essentially of a sequence encoding a moderated nitrate reductase enzyme;

(ii) a polypeptide encoded by the polynucleotide according to (i), (iii) a polypeptide containing a moderated nitrate reductase enzyme, consisting of a moderated nitrate reductase enzyme, or consisting essentially of a moderated nitrate reductase enzyme; or (iv) a construct, a vector, or an expression vector containing the polynucleotide according to (i), and the expression or the activity of the nitrate reductase is moderated as compared with a control unmodified tobacco plant, and the moderated nitrate reductase enzyme is (a) a nitrate reductase polypeptide including amino acid substitution at a position corresponding to position 523 of SEQ ID NO: 4 or (b) a nitrate reductase polypeptide including amino acid substitution at a position corresponding to position 523 of SEQ ID NO: 4, and is modified so that the amino acid at position 523 of SEQ ID NO: 4 is substituted with aspartic acid.

The Examples of PTL 1 discloses data on a decrease in the amount of nitric acid in the leaves of the S523D mutant and data on a decrease in TSNA in the cured leaves and smoke as to the S523D mutant of the nitrate reductase gene (Nia2) of tobacco. The S523D mutant in the Examples of the literature constitutively expresses S523D mutated Nia2 under the 35S promoter.

WO 2020/141062 (PTL 2) describes mutants in which the methionine residue at position 527 of the nitrate reductase protein of tobacco is substituted with other amino acid residues. The Examples of PTL 2 describes a decrease in the amount of nitric acid in the leaves of the M527I mutant (only the homozygous type) of the nitrate reductase gene (Nia2) of tobacco.

CITATION LIST

Patent Literature

PTL 1: International Publication No. WO 2016/046288
PTL 2: International Publication No. WO 2020/141062

Non Patent Literature

NPL 1: The Plant Cell, 8(1996), 505-517
NPL 2: Plant physiology., 140(2006), 1085-1094
NPL 3: Plant J., 35(2003), 566-573
NPL 4: Planta 219(2004), 59-65
NPL 5: Heisei 23-nen Nihonshokubutsubyorigakkai Taikai P258, (226) Tabako Henitai Paneru no Sakushutsu (The Convention of the Phytopathological Society of Japan in 2011 P258, (226) Production of Tobacco Mutant Panel)

SUMMARY OF INVENTION

Technical Problem

The S523D recombinant of NPLs 2 and 3 and PTL 1 constitutively expresses the Nia2 gene having amino acid substitution mutation under the 35S promoter. When the present applicant has confirmed, it has been revealed that this gene recombinant is accompanied with seriously defective vegetation. PTL 2 discloses that it is considered that when M527 is mutated into I, the position is easily phosphorylated, and the NR activity therefore decreases. Nevertheless, no reason for a decrease in the nitric acid content is described. No heterozygote having the mutation heterozygously is disclosed. As to the Nia1 gene, no mutant, no gene-modified mutant, or no gene recombinant are obtained in any of the prior art literatures.

Proline 525 (P525) of the nitrate reductase protein of the tobacco plant is located at the plus 2 position from the serine 523 (S523), which is a phosphorylation site. It is known that this proline is widely conserved in plants (FIG. 8 of NPL 1), but it was shown that the modification of this proline into alanine did not have a great influence on the recognition by NR kinase (Table 3 of NPL 1).

However, the present inventors have produced many mutants into which the two nitrate reductases NIA1 and NIA2 are mutated in tobacco plants, found that tobacco plants containing the nitrate reductases in which the amino acid residues corresponding to position 525 in the amino acid sequences of the nitrate reductase proteins are mutated from proline to amino acid residues other than proline have properties excellent in that (a) the activities of the nitrate reductases hardly decrease even under a dark condition, (b) the individual is essentially equivalent to the control in growth, and (c) nitric acid decreases as compared with the control, and thought of the present invention.

Solution to Problem

The present invention includes, but is not limited to, the following embodiments.

Embodiment 1

A tobacco plant containing nitrate reductase in which an amino acid residue corresponding to position 525 in an amino acid sequence corresponding to SEQ ID NO: 2 or 4 is mutated from proline to an amino acid residue other than proline.

Embodiment 2

The tobacco plant according to embodiment 1, wherein the tobacco plant has one or more properties of the following (a) to (c):

(a) activity of the nitrate reductase under a dark condition is 80% or more of activity of the nitrate reductase under a light condition;

(b) an individual is essentially equivalent to a control in growth; and/or (c) nitric acid decreases as compared with the control, wherein the control is a tobacco plant containing nitrate reductase consisting of the amino acid sequence of SEQ ID NO: 2 or 4.

Embodiment 3

The tobacco plant according to embodiment 1 or 2, containing: nitrate reductase in which the amino acid residue corresponding to position 525 in the amino acid sequence corresponding to SEQ ID NO: 2 or 4 is mutated from proline to leucin or serine.

Embodiment 4

The tobacco plant according to any one of embodiments 1 to 3, wherein an amino acid residue corresponding to position 523 in the amino acid sequence corresponding to SEQ ID NO: 2 or 4 is serine in the amino acid sequence of the mutated nitrate reductase.

Embodiment 5

The tobacco plant according to any one of embodiments 1 to 4, wherein the mutated nitrate reductase has an amino acid sequence that is 80% or more identical with the amino acid sequence of SEQ ID NO: 2 or 4.

Embodiment 6

The tobacco plant according to any one of embodiments 1 to 5, wherein the mutated nitrate reductase has an amino acid sequence corresponding to any one of SEQ ID Nos: 5 to 8.

Embodiment 7

The tobacco plant according to any one of embodiments 2 to 6, wherein nitric acid decreases by at least 10% as compared with the control.

Embodiment 8

The tobacco plant according to any one of embodiments 1 to 7, wherein the tobacco plant is a mutant, or is a gene-modified variant.

Embodiment 9

The tobacco plant according to any one of embodiments 1 to 8, wherein the tobacco plant is *Nicotiana tabacum.*

Embodiment 10

A method for producing the tobacco plant according to any one of embodiments 1 to 9, including:

(i) modifying an amino acid residue corresponding to position 525 in an amino acid sequence corresponding to SEQ ID NO: 2 or 4 of nitrate reductase of a tobacco plant from proline to an amino acid residue other than proline or (ii) selecting a tobacco plant in which an amino acid residue corresponding to position 525 in an amino acid sequence corresponding to SEQ ID NO: 2 or 4 of nitrate reductase is mutated from proline to an amino acid residue other than proline by mutation.

Embodiment 11

Leaf tobacco harvested from the tobacco plant according to any one of embodiments 1 to 9.

Embodiment 12

A cured leaf generated from the leaf tobacco according to embodiment 11.

Embodiment 13

A cut filler, powder, a sheet, a stem, granules, or an extract produced from the cured leaf according to embodiment 12.

Embodiment 14

A tobacco product containing the cured leaf according to embodiment 12 and/or the cut filler, the powder, the sheet, the stem, the granules, or the extract according to embodiment 13.

Advantageous Effects of Invention

A modified tobacco plant of the present invention decreases in the amount of nitrates accumulated in leaves. The modified tobacco plant of the present invention can be utilized to reduce the TSNAs of a tobacco raw material or a tobacco product. The modified tobacco plant of the present invention not only has a decreased amount of nitric acid in leaves, but also preferably exhibits good plant growth. This is also an excellent remarkable effect for utilization as a material of leaf tobacco for producing a tobacco product.

DESCRIPTION OF EMBODIMENTS

Figure 1:
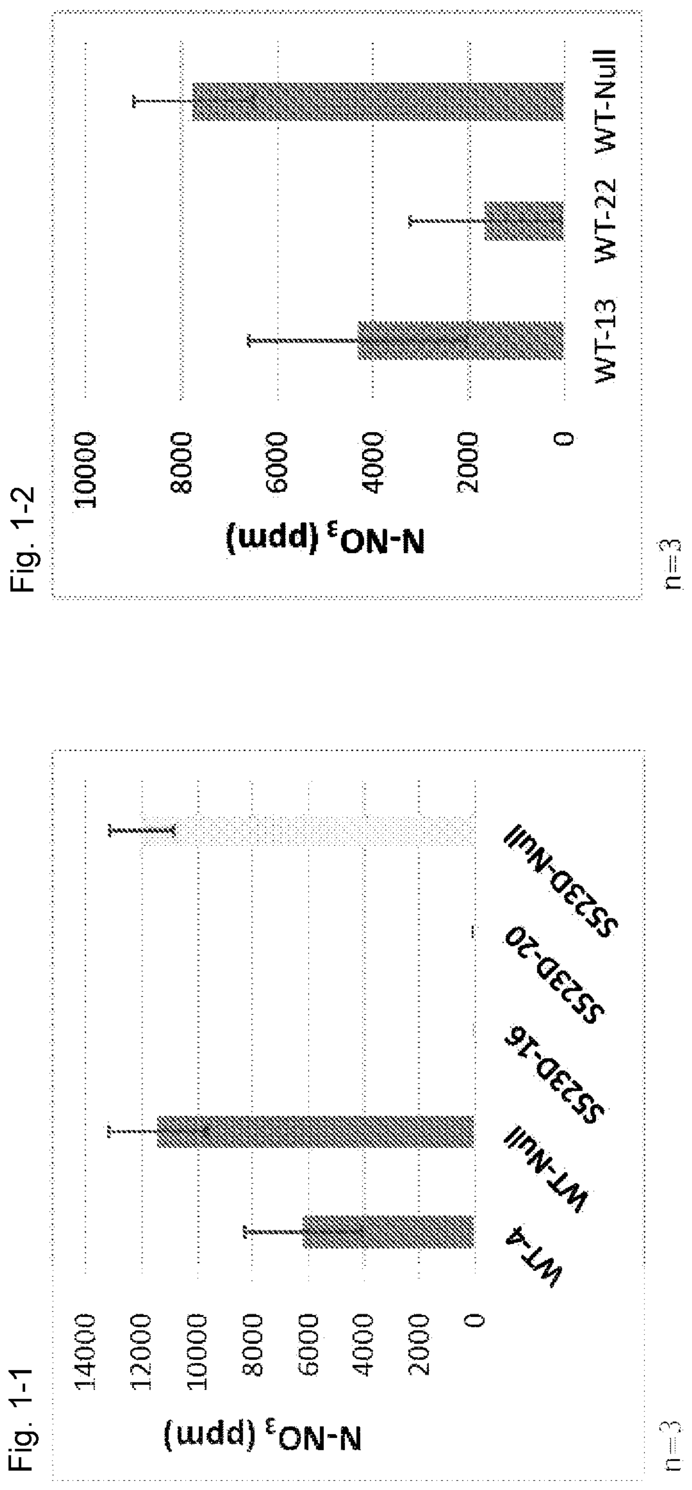
FIG. 1 is figures showing the amounts of nitric acid in leaves (laminas) constitutively expressing NIA2 having S523D mutation (NIA2_S523D) and wild type NIA2 (NIA2_WT). S523D-16 and S523-20 are two lines of T1 generation derived from different T0 individuals. WT-4, WT-13, and WT-22 are three lines of T1 generation derived from different T0 individuals. S523D-Null and WT-Null are results of leaves of lines of T1 generation that are recombinants into which NIA2 S523D and NIA2 WT are transformed, respectively, and do not express NIA2 S523D or NIA2_WT. The number of replications is 3, and the error bars indicate standard deviations.

The present invention includes the following embodiments unlimitedly. Technical and scientific terms used herein have the same meanings as meanings that those skilled in the art usually understand unless otherwise specified. Substances, materials, and examples disclosed herein are mere illustrations, and are not intended to limit the present invention. When things "in one embodiment" is mentioned herein, it is meant that the things are not limited to the embodiment, namely that the things are unlimited.

1. Tobacco Plant

In one embodiment, the present invention relates to a tobacco plant. The tobacco plant of the present invention contains nitrate reductase in which an amino acid residue corresponding to position 525 in an amino acid sequence corresponding to SEQ ID NO: 2 or 4 is mutated from proline to an amino acid residue other than proline (hereinafter occasionally referred to as "mutated nitrate reductase").

In one embodiment, the "tobacco plant" is a plant of Solanaceae *Nicotiana. Examples include Nicotiana acaulis, Nicotiana acuminata, Nicotiana acuminata* var. *multzjlora, Nicotiana africana, Nicotiana alata, Nicotiana amplexicaulis, Nicotiana arentsii, Nicotiana attenuata, Nicotiana benavidesii, Nicotiana benthamiana, Nicotiana bigelovii, Nicotiana bonariensis, Nicotiana cavicola, Nicotiana clevelandii, Nicotiana cordifolia, Nicotiana corymbosa,*

*Nicotiana debneyi, Nicotiana excelsior, Nicotiana forgetiana, Nicotiana fragrans, Nicotiana glauca, Nicotiana glutinosa, Nicotiana goodspeedii, Nicotiana gossei, Nicotiana ingulba, Nicotiana kawakamii, Nicotiana knightiana, Nicotiana langsdorfi, Nicotiana linearis, Nicotiana longiflora, Nicotiana maritima, Nicotiana megalosiphon, Nicotiana miersii, Nicotiana noctiflora, Nicotiana nudicaulis, Nicotiana obtusifolia, Nicotiana occidentalis, Nicotiana occidentalis* subsp. *Hesperis, Nicotiana otophora, Nicotiana paniculata, Nicotiana pauczjlora, Nicotiana petunioides, Nicotiana plumbaginifolia, Nicotiana quadrivalvis, Nicotiana raimondii, Nicotiana repanda, Nicotiana rosulata, Nicotiana rosulata* subsp. *Ingulba, Nicotiana rotundifolia, Nicotiana rustica* (wild tobacco), *Nicotiana setchellii, Nicotiana simulans, Nicotiana solanifolia, Nicotiana spegazzinii, Nicotiana stocktonii, Nicotiana suaveolens, Nicotiana sylvestris, Nicotiana tabacum, Nicotiana thyrsiflora, Nicotiana tomentosa, Nicotiana tomentosiformis, Nicotiana trigonophylla, Nicotiana umbratica, Nicotiana undulata, Nicotiana velutina, Nicotiana wigandioides*, and hybrids of *Nicotiana* plants. Although the tobacco plant is not limited, *Nicotiana Benthamiana, Nicotiana rustica*, and *Nicotiana tabacum* are more preferable, and *Nicotiana rustica* and *Nicotiana tabacum* to be used as raw materials for leaf tobacco production are particularly preferable.

The tobacco plant can include not only an matured and the whole of the tobacco plant but also portions thereof. The portions are unlimitedly selected from the group consisting of leaves (including laminas and petioles), stems, roots, seeds, flowers, pollens, anthers, ovules, pedicels, meristematic tissues, cotyledons, hypocotyls, pericycles, embryos, albumens, explants, calluses, tissue cultures, sprouts, cells, and protoplast.

"Nitrate reductase" (occasionally also referred to as "NR") means an enzyme that is one of nitrogen metabolism enzymes, and reduces nitric acid ($NO_3$—) to nitrous acid ($NO_2$—). Nitrate reductase is widely distributed among plants, yeast, fungi, algae, and the like. Nitrate reductases are known in tobacco, *Arabidopsis thaliana*, rape, haricot beans, barley, pumpkin, birch, soy, corn, rice, spinach, and the like among plants (Table 8 in NPL 1).

In one embodiment, the nitrate reductase is derived from a plant, preferably from a plant of *Nicotiana*. In one embodiment, the nitrate reductase is nitrate reductase of *Nicotiana tabacum. Nicotiana tabacum* has two nitrogen metabolism enzyme genes referred to as Nia1 and Nia2 and having high homology. In one embodiment, the nitrate reductase herein includes NIA1 protein (the Nia1 gene is derived from the T genome) and mutants thereof or/and NIA2 protein (the Nia2 gene is derived from the S genome) and mutants thereof. In one embodiment, the nitrate reductase herein includes NIA1 protein (the Nia1 gene is derived from the T genome) and mutants thereof.

The Nia1 gene and the Nia2 gene have nucleotide sequences of SEQ ID NOs: 1 and 3, respectively. The NIA1 protein and the NIA2 protein have amino acid sequences of SEQ ID NOs: 2 and 4 encoded by the nucleotide sequences of the SEQ ID NOs: 1 and 3, respectively.

The tobacco plant of the present invention includes nitrate reductase in which an amino acid residue corresponding to position 525 in the amino acid sequence corresponding to SEQ ID NO: 2 or 4 is mutated from proline to an amino acid residue other than proline. "Containing nitrate reductase" herein means that containing the nitrate reductase protein or containing the nucleic acid encoding the nitrate reductase protein unless otherwise specified. The amino acid sequence at positions 518 to 528 of the amino acid sequence corresponding to SEQ ID NO: 2 or 4 is "LKKSISTPFMN". The nitrate reductase proteins of plants other than *Nicotiana tabacum* also contain a site having an amino acid sequence that is similar to the amino acid sequence "LKKSISTPFMN" at positions 518 to 528 of the amino acid sequence corresponding to SEQ ID NO: 2 or 4. The site may include some mutations, and, for example, Table 8 in NPL 1 mentions that the nitrate reductase proteins of plants have the amino acid sequence "LK(K/R)(S/T)(I/V/T/A)S(T/S)PFMN" at positions 518 to 528 of the amino acid sequence corresponding to SEQ ID NO: 2 or 4. For example, the "amino acid residue corresponding to position 525 in the amino acid sequence corresponding to SEQ ID NO: 2 or 4" is a wild type amino acid residue following S-(T/S) of the nitrate reductase protein and is an amino acid residue followed by F-M in the wild type nitrate reductase protein, and is proline in the wild type nitrate reductase protein.

In the tobacco plant of the present invention, proline at position 525 in the protein of the wild type nitrate reductase is mutated into an amino acid residue other than proline. The mutation in the nitrate reductase gene may be heterozygous or homozygous. If two nitrate reductase proteins that are the NIA1 protein and the NIA2 protein exist, either of the NIA1 protein or the NIA2 protein may have the mutation.

In one embodiment, the tobacco plant contains nitrate reductase in which an amino acid residue corresponding to position 525 in the amino acid sequence corresponding to SEQ ID NO: 2 or 4 is mutated from proline to leucin or serine.

In one embodiment, in the amino acid sequence of the mutated nitrate reductase, an amino acid residue corresponding to position 523 in the amino acid sequence corresponding to SEQ ID NO: 2 or 4 is serine. This means that the amino acid residue at this position is not mutated from the amino acid residue of wild type nitrate reductase (and also that the amino acid residue is not modified).

In one embodiment, in the amino acid sequence of the mutated nitrate reductase, an amino acid residue corresponding to position 527 in the amino acid sequence corresponding to SEQ ID NO: 2 or 4 is methionine. This means that the amino acid residue at this position is not mutated from the amino acid residue of wild type nitrate reductase (and also that the amino acid residue is not modified).

As long as the condition that the mutated nitrate reductase of the present invention is nitrate reductase in which the amino acid residue corresponding to position 525 in the amino acid sequence corresponding to SEQ ID NO: 2 or 4 is mutated from proline to an amino acid residue other than proline, and preferably, an amino acid residue corresponding to position 523 in the amino acid sequence corresponding to SEQ ID NO: 2 or 4 is serine in the amino acid sequence is satisfied, the mutated nitrate reductase may be a mutant having slight variety (mutation) in SEQ ID NO: 2 or 4.

In one embodiment, the mutated nitrate reductase has an amino acid sequence that is 80% or more identical with the amino acid sequence of SEQ ID NO: 2 or 4. Preferably, the amino acid sequence is 82% or more, 85% or more, 88% or more, 90% or more, 92% or more, 95% or more, 97% or more, 98% or more, or 99% or more identical with the amino acid sequence of SEQ ID NO: 2 or 4. In any case, the condition that the amino acid residue corresponding to position 525 in the amino acid sequence corresponding to SEQ ID NO: 2 or 4 is mutated from proline to an amino acid residue other than proline is satisfied.

In one embodiment, the mutated nitrate reductase is encoded by a nucleic acid having a nucleotide sequence that is 80% or more identical with the nucleotide sequence corresponding to SEQ ID NO: 1 or 3. Preferably, the mutated nitrate reductase is encoded by a nucleic acid having a nucleotide sequence that is 82% or more, 85% or more, 88% or more, 90% or more, 92% or more, 95% or more, 97% or more, 98% or more, or 99% or more identical with the nucleotide sequence of SEQ ID NO: 1 or 3. In any case, the condition that the amino acid residue corresponding to position 525 in the amino acid sequence corresponding to SEQ ID NO: 2 or 4 is mutated from proline to an amino acid residue other than proline is satisfied.

The identity % between two amino acid sequences can be determined by visual inspection and mathematical calculation herein. The identity % can be determined using a computer program. Examples of such a computer program include BLAST and ClustalW.

Especially various conditions (parameters) for identity retrieval by the BLAST program is described by Altschul et al. (Nucl. Acids. Res., 25, p.3389-3402, 1997), and can be obtained publicly from the web sites of the NCBI and the DNA Data Bank of Japan (DDBJ) (BLAST manual, Altschul et al. NCB/NLM/NIH Bethesda, MD20894; Altschul et al.). The identity % can also be determined using a program such as Genetic information processing software GENETYX Ver. 7 (GENETYX CORPORATION), DNASIS Pro (Hitachi Solutions, Ltd.), or Vector NTI (Infomax).

The identity % between two nucleotide sequences can be determined by visual inspection and mathematical calculation herein. The identity % can be determined using a computer program. Examples of such a sequence comparison computer program include the BLASTN program (Altschul et al. (1990) J. Mol. Biol. 215: p.403-10): Version 2.2.7 that is available from the web site of the United States National Library of Medicine: https://blast.ncbi.nlm.nih.gov/Blast.cgi or the WU-BLAST 2.0 algorithm. The setting of the standard default parameters of WU-BLAST 2.0 described in the following Internet sites: http://blast.wustl.edu can be used.

In one embodiment, the mutated nitrate reductase may have an amino acid sequence in which one or several amino acids are deleted, substituted, inserted, or added in the amino acid sequence of SEQ ID NO: 2 or 4. However, the nitrate reductase satisfies the condition that the amino acid residue corresponding to position 525 in the amino acid sequence corresponding to SEQ ID NO: 2 or 4 is mutated from proline to an amino acid residue other than proline.

The amino acid sequence in which "one or several amino acids are deleted, substituted, inserted, or added" means an amino acid sequence in which one or several amino acids are deleted, one or several amino acids are substituted with other amino acids, other amino acids are inserted, and/or other amino acids are added in a target amino acid sequence. The "several amino acids" unlimitedly means 200 or less, 100 or less, 50 or less, 30 or less, 20 or less, 15 or less, 12 or less, 10 or less, 8 or less, 6 or less, 4 or less, 3 or less, or 2 or less amino acid. Alternatively, the several amino acids mean amino acids corresponding to 30%, preferably 25%, 20%, 15%, 10%, 5%, 3%, 2% or 1% of the full length of the amino acid sequence.

Among the above, the substitution is preferably conservative substitution. The conservative substitution is to substitute a specific amino acid residue with a residue having similar physicochemical characteristics. If the characteristics of the original sequence structure are not changed substantially, any substitution may be performed. For example, if the substituted amino acid does not destroy a helix existing in the original sequence, or does not destroy other types of secondary structures characterizing the original sequence, any substitution may be performed. Although the conservative substitution of amino acid residues is exemplified below by classifying amino acids into the groups of substitutable amino acid residues, the substitutable amino acid residues are not limited to the substitutable amino acid residues described below.

Group A: leucin, isoleucine, valine, alanine, methionine, glycine, cysteine, and proline Group B: aspartic acid and glutamic acid Group C: asparagine and glutamine Group D: lysine and arginine Group E: serine and threonine Group F: phenylalanine, tyrosine, tryptophan, and histidine In the case of unconservative substitution, among the above-mentioned types, one member can be replaced with another type of member. For example, amino acids in the above-mentioned B, D, and E groups may be substituted with amino acids in other groups than those to remove unprepared sugar chain modification. Alternatively, cysteine may be deleted, or may be substituted with another amino acid to prevent the cysteine from being folded in a protein in the tertiary structure. Alternatively, amino acids may be substituted in view of the amino acid hydropathy indices (J. Kyte and R. Doolittle, J. Mol. Biol., Vol. 157, p. 105-132, 1982), which are indices to the hydrophobicity/hydrophilicity of the amino acids, so that the balance between the hydrophilicity and the hydrophobicity is kept, or so that he hydrophilicity is increased to facilitate the synthesis.

As another embodiment, the substitution with an amino acid having little steric hindrance than the original amino acid, for example, substitution from the group F to the group A, B, C, D or E; and the substitution from a charged amino acid to an uncharged amino acid, for example, the substitution from the group B to the group C, may be performed.

In one embodiment, the mutated nitrate reductase has an amino acid sequence corresponding to any one of SEQ ID NOs: 5 to 8. SEQ ID NOs: 5 and 6 are amino acid sequences in which the amino acid residue corresponding to position 525 in an amino acid sequence corresponding to SEQ ID NO: 2 or 4 is mutated from proline to leucin, respectively. SEQ ID NOs: 7 and 8 are amino acid sequences in which the amino acid residue corresponding to position 525 in the amino acid sequence corresponding to SEQ ID NO: 2 or 4 are mutated from proline to serine, respectively.

In one embodiment, the tobacco plant may be a mutant, or may be a gene-modified variant.

The "mutant" herein is a modified variant of the tobacco plant by random mutation caused naturally or artificially. A technique for producing a mutant is described in detail in the following "3. Method for producing tobacco plant". Although the mutant is not limited, the mutant may be a tobacco plant obtained by selecting a tobacco plant having a nucleic acid encoding a nitrate reductase protein in which the amino acid residue corresponding to position 525 in the amino acid sequence corresponding to SEQ ID NO: 2 or 4 is mutated from proline to an amino acid residue other than proline from posterity obtained by crossbreeding a mutant as a parent with a tobacco plant; or the posterity thereof.

The "gene-modified variant" is a tobacco plant having a modified endogenous gene encoding a nitrate reductase protein to express the amino acid residue corresponding to position 525 in the amino acid sequence corresponding to SEQ ID NO: 2 or 4 is mutated from proline to an amino acid residue other than proline, and includes the posterity thereof.

The "mutant" and the "gene-modified variant" can include not only an adult and the whole of the tobacco plant but also portions thereof. The portions are unlimitedly selected from the group consisting of leaves (including laminas and petioles), stems, roots, seeds, flowers, pollens, anthers, ovules, pedicels, meristematic tissues, cotyledons, hypocotyls, pericycles, embryos, albumens, explants, calluses, tissue cultures, sprouts, cells, and protoplast.

In one embodiment, the tobacco plant may be a gene recombinant having, introduced by artificial procedure, the nucleic acid encoding a nitrate reductase protein in which the amino acid residue corresponding to position 525 in the amino acid sequence corresponding to SEQ ID NO: 2 or 4 is mutated from proline to an amino acid residue other than proline, to express the protein, and the posterity thereof. Although the nucleic acid encoding the protein is not limited, the nucleic acid is preferably integrated in the genome stably so that the nucleic acid is passed down to the posterity.

2. Properties of Tobacco Plant

The tobacco plant of the present invention unlimitedly has one or more properties of the following (a) to (c):

(a) the activity of nitrate reductase under the dark condition is 80% or more of the activity of the nitrate reductase under the light condition;
(b) the individual is essentially equivalent to the control in growth; and/or
(c) nitric acid decreases as compared with the control.

Here, the control is a tobacco plant containing nitrate reductase consisting of the amino acid sequences of SEQ ID NO: 2 or 4. The nitrate reductase consisting of the amino acid sequence of SEQ ID NO: 2 or 4 is nitrate reductase that a wild type tobacco plant has, and is not modified at all. In one embodiment, the control may be *Nicotiana tabacum* containing the nitrate reductase consisting of the amino acid sequences of SEQ ID NO: 2 or 4, preferably wild type *Nicotiana tabacum*. The wild type *Nicotiana tabacum* contains the nitrate reductase consisting of the amino acid sequence of SEQ ID NO: 2 or 4, and neither the expression nor the activity thereof is modified at all.

In one embodiment, the tobacco plant of the present invention has two or more properties or all the three properties of (a) to (c).

The "activity of nitrate reductase" can be unlimitedly measured, for example, by a technique described in "(5) NR enzyme activity" of Comparative Example 2 herein. For example, the tissues of collected leaves (laminas) of the tobacco plant are freeze-dried to prepare crude extract liquid. An NR activity measurement buffer is added to this crude extract liquid for reaction, and the amount of nitrous acid generated in reaction liquid is measured.

Besides, the "activity of nitrate reductase" can be measured by a method for measuring the absorbance at 340 nm using 0.5 mM potassium ferricyanide and 0.1 mM NADH, a method for measuring the oxidation of reduced methyl viologen or bromophenol blue using reduced methyl viologen or bromophenol blue instead of the quantification of nitrous acid, or the like.

That is, although the "activity of nitrate reductase" herein is not limited, the "activity of nitrate reductase" may be activity measured with respective to the tissue of a target tobacco plant by the above-mentioned techniques and methods.

The dark condition unlimitedly means placing a tobacco plant under the condition that light does not reach the tobacco plant (for example, at an illuminance of 1 lux or less, preferably 0.1 luxes or less) for 30 minutes or more, 60 minutes or more, 90 minutes or more, or 120 minutes or more. Meanwhile, the light condition means placing a tobacco plant under the condition that light reaches the tobacco plant (for example, at an illuminance of 5000 luxes or more, preferably 10000 luxes or more) for 30 minutes or more, 60 minutes or more, 90 minutes or more, or 120 minutes or more.

"The activity of the nitrate reductase under the dark condition is 80% or more of the activity of the nitrate reductase under the light condition" means that the activity of the nitrate reductase under the dark condition is 80% or more of the activity of the nitrate reductase under the light condition measured by the same method under the same conditions except the condition of light. The activity of the nitrate reductase under the dark condition is unlimitedly preferably 85% or more, 88% or more, 90% or more, 92% or more, 95% or more, 97% or more, 98% or more, or 99% or more of the activity of the nitrate reductase under the light condition. In one embodiment, the activity of the nitrate reductase under the dark condition does not decrease as compared with the activity of the nitrate reductase under the light condition substantially, or is substantially the same. In one embodiment, the activity of the nitrate reductase under the dark condition is the same as the activity of the nitrate reductase under the light condition. In the tobacco plant containing the nitrate reductase consisting of the amino acid sequences of SEQ ID NO: 2 or 4 (control), the activity of the nitrate reductase is suppressed under the dark condition as compared with under the light condition. Meanwhile, in the tobacco plant containing the nitrate reductase in which the amino acid residue corresponding to position 525 in the amino acid sequence corresponding to SEQ ID NO: 2 or 4 is mutated from proline to an amino acid residue other than proline, the activity of the nitrate reductase is not or hardly suppressed even under the dark condition in the same way as under the light condition. In one embodiment, with respect to the mutation of the nitrate reductase gene, the activity of the nitrate reductase under the dark condition hardly decreases in not only the mutated homozygote but also the mutated heterozygote.

In one embodiment, the tobacco plant contains the nitrate reductase consisting of the amino acid sequence of SEQ ID NO: 2 or 4, and the individual is essentially equivalent to the control that is a tobacco plant in growth.

Figure 3:
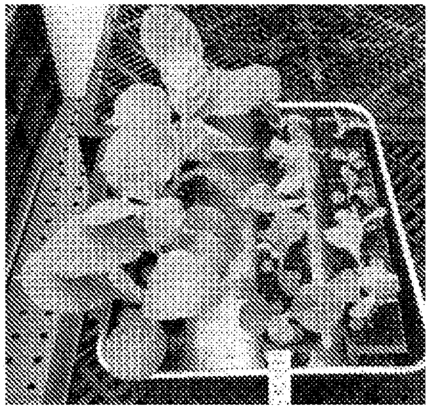
FIG. 3 is a photographic figure of the initial development of a S523D-16 recombinant (plant body constitutively expressing NIA2 having S523D mutation (NIA2_S523D)) and Null (separated line that does not express NIA2_S523D, T2 generation) (eleventh day after temporary planting).

As shown in Comparative Example 2 herein, a great difference was not seen in vegetation regardless of the presence or absence of the constitutive expression in the wild type NIA2_WT. The recombinant tobacco constitutively expressing NIA2_S523D and described in PTL 1 exhibited dwarfism, in which the individual size decreases (FIG. 3). In Example 6, marked defective vegetation was observed, and the anthesis was also furthermore late in the line constitutively expressing NIA2_S523D as compared with the line that did not express.

Meanwhile, the tobacco plant containing the nitrate reductase in which the amino acid residue corresponding to position 525 in the amino acid sequence corresponding to SEQ ID NO: 2 or 4 was mutated from proline to an amino acid residue other than proline was essentially equivalent to the control that was a tobacco plant containing the nitrate reductase consisting of the amino acid sequence of SEQ ID NO: 2 or 4 in the growth of the individual. In Example 6, in lines in which the amino acid substitution mutation of P525L and P525S in NIA1 was homozygous, the abnormal vegetation was not observed, either.

"The individual is essentially equivalent in growth" means that the sizes (growing) such as the height, the number of leaves, and the sizes of leaves of the plant body; the mass (for example, the dry matter weight of leaves above the ground (biomass)); the anthesis; and the like of the individual are substantially equivalent. It is unlimitedly meant that, for example, when the heights are compared, the difference therebetween is 20% or less, 15% or less, 10% or less, or 5% or less.

In one embodiment, the amount of nitric acid contained in the tobacco plant decreases as compared with the control. Nitric acid can be unlimitedly measured, for example, by the technique described in (2) Nitric acid quantification of Comparative Example 2 herein. For example, leaves collected from the tobacco plant are cured, followed by extraction with water, and the filtered filtrate may be then used as a measurement sample.

In one embodiment, nitric acid preferably decreases in the tobacco plant by at least 10%, at least 15%, at least 20%, at least 25%, at least 30%, at least 35%, at least 40%, at least 45%, or at least 50% as compared with the control.

The one or more properties of the above-mentioned (a) to (c) is preferably inherited in not only M1 generation that is a mutant or a gene-modified variant but also the passage subsequent thereto (M2 generation, M3 generation, and the generation subsequent thereto).

3. Method for Producing Tobacco Plant

In one embodiment, the present invention relates to a method for producing a tobacco plant. The method for producing a tobacco plant includes:

(i) modifying an amino acid residue corresponding to position 525 in an amino acid sequence corresponding to SEQ ID NO: 2 or 4 of nitrate reductase of a tobacco plant from proline to an amino acid residue other than proline or (ii) selecting a tobacco plant in which an amino acid residue corresponding to position 525 in an amino acid sequence corresponding to SEQ ID NO: 2 or 4 of nitrate reductase is mutated from proline to an amino acid residue other than proline by mutation.

The meanings of "nitrate reductase", the "mutation of the amino acid residue corresponding to position 525 in the amino acid sequence corresponding to SEQ ID NO: 2 or 4 from proline to an amino acid residue other than proline", and the like are as described in "2. Properties of tobacco plant" and the part previous thereto.

An amino acid residue corresponding to position 525 in an amino acid sequence corresponding to SEQ ID NO: 2 or 4 in a nitrate reductase protein in a tobacco plant can be modified from proline to an amino acid residue other than proline by modifying an endogenous gene encoding the nitrate reductase protein in which the amino acid residue corresponding to position 525 in the amino acid sequence corresponding to SEQ ID NO: 2 or 4 is mutated from proline to an amino acid residue other than proline so that the tobacco plant expresses the protein.

For example, the endogenous gene may be modified using a genome editing system. The genome editing system can bind or cleave the endogenous nitrate reductase gene at a specific position to produce the nitrate reductase protein having mutation at position 525 in the amino acid sequence corresponding to SEQ ID NO: 2 or 4. The endogenous nitrate reductase gene can be modified with the genome editing system containing a site-specific nuclease that binds and cleaves the endogenous nitrate reductase gene. The genome editing system can also use nuclease-interposed non-homologous end joining or homologous recombination repair. The site-specific nuclease can be modified. For example, the modified site-specific nuclease may be the CRISPR/Cas9 system, ZFN, or TALEN. The site-specific nuclease can bind and cleave the endogenous nitrate reductase gene. As the genome editing system, a modified CRISPR/Cas system such as a modified CRISPR/Cas-9 system, modified transcription activator-like effector nuclease, modified zinc finger nuclease, or modified meganuclease may be used.

The method for producing the tobacco plant may include a step of selecting the tobacco plant in which an amino acid residue corresponding to position 525 in an amino acid sequence corresponding to SEQ ID NO: 2 or 4 of nitrate reductase protein is mutated from proline to an amino acid residue other than proline by mutation.

Means for causing mutation in a plant is well-known in the art, and mutation can be caused in a nitrate reductase gene that a plant has mainly using a mutagen for causing a point mutation and short deletion, insertion, transversion, and/or transfer including a chemical mutagen or radiation. The chemical mutagen includes, but is not limited to, ethyl methanesulfonate, methyl methanesulfonate, N-ethyl-N-nitrosourea, triethylmelamine, N-methyl-N-nitrosourea, procarbazine, chlorambucil, cyclophosphamide, diethyl sulfate, an acrylamide monomer, melphalan, nitrogen mustard, vincristine, dimethylnitrosamine, N-methyl-N'-nitro-nitrosoguanidine, nitrosoguanidine, 2-aminopurine, 7,12-dimethyl-benz(a)anthracene, ethylene oxide, hexamethylphosphoramide, bisulfane, diepoxyalkanes (diepoxyoctane, diepoxybutane, and substances similar thereto), 2-methoxy-6-chloro-9[3-(ethyl-2-chloroethyl)aminopropylamino]acridine dihydrochloride, and formaldehyde. The radiation includes, but is not limited to, a γ-rays, heavy ion beams, X-rays, neutron beams, or UV.

The step of selecting the tobacco plant in which the amino acid residue corresponding to position 525 in the amino acid sequence corresponding to SEQ ID NO: 2 or 4 of the nitrate reductase protein is mutated from proline to an amino acid residue other than proline by mutation may include one or more crossbreeding steps. In one embodiment, a seed from a plant body is mutagenized, then sown, and cultivated to obtain a first-generation plant body, and the second-generation plant bodies obtained by self-pollinating this may be screened for mutants. The screening of the second-generation plant bodies is advantageous in that the mutation is mutation derived from reproductive cells. Although the object to be mutagenized is not limited, the object may be seeds or pollen. When pollen is mutagenized, plant bodies raised from seeds obtained by crossbreeding the pollen with a plant body that is not mutagenized may be screened for mutants.

The method for producing the tobacco plant can be performed by introducing a nucleic acid encoding a nitrate reductase protein in which an amino acid residue corresponding to position 525 in the amino acid sequence corresponding to SEQ ID NO: 2 or 4 is mutated from proline to an amino acid residue other than proline into a tobacco plant by artificial operation so that the tobacco plant expresses the protein.

The method for introducing a nucleic acid is not particularly limited, and can be performed using a well-known method for introducing a nucleic acid. For example, a physicochemical method (method for introducing DNA directly) such as the polyethylene glycol method (the PEG method), electroporation, the particle gun method, microinjection, or the whisker method or a biological method (method for introducing DNA indirectly) such as the *Agrobacterium* method can be preferably used.

A target gene-modified variant, a mutant, or a gene recombinant with a modified amino acid residue corresponding to position 525 in the amino acid sequence corresponding to SEQ ID NO: 2 or 4 can be selected unlimitedly, for example, by extracting the genomic DNA from a tobacco plant, amplifying the DNA by PCR or the like, and analyzing the nucleotide sequence of the DNA encoding a portion containing the amino acid residue corresponding to position 525 in the amino acid sequence corresponding to SEQ ID NO: 2 or 4. Besides, the method can be selected from a method for detecting a difference between sequences using a difference between electrophoretic distances by the SSCP (single strand conformation polymorphism) method, a method for detecting the presence or the absence of mutation by cleaving a mismatch site using T7 endonuclease I or the like, and the like.

In one embodiment, the present invention may be a nucleic acid selection marker to be used for selecting a tobacco plant containing nitrate reductase in which an amino acid residue corresponding to position 525 in an amino acid sequence corresponding to SEQ ID NO: 2 or 4 is mutated from proline to an amino acid residue other than proline. Alternatively, the present invention may be a detection polynucleotide to be used for detecting the mutation of the amino acid residue corresponding to position 525 in the amino acid sequence corresponding to SEQ ID NO: 2 or 4 of the nitrate reductase from proline to an amino acid residue other than proline. The nucleic acid selection marker or the detection polynucleotide may be unlimitedly a nucleic acid amplification primer for amplifying the nucleotide sequence of the DNA encoding a portion containing the amino acid residue corresponding to position 525 in the amino acid sequence corresponding to SEQ ID NO: 2 or 4, a primer for sequencing nucleotide sequence of the DNA encoding a portion containing the amino acid residue corresponding to position 525 in the amino acid sequence corresponding to SEQ ID NO: 2 or 4, or a probe to be bound to the DNA encoding a portion containing the amino acid residue corresponding to position 525 in the amino acid sequence corresponding to SEQ ID NO: 2 or 4. Those skilled in the art can suitably select these nucleic acid selection marker or detection polynucleotide based on well-known techniques.

In one embodiment, the present invention may be a kit containing a nucleic acid selection marker to be used for selecting a tobacco plant containing the nitrate reductase in which the amino acid residue corresponding to position 525 in an amino acid sequence corresponding to SEQ ID NO: 2 or 4 is mutated from proline to an amino acid residue other than proline or a detection polynucleotide to be used for detecting the mutation of the amino acid residue corresponding to position 525 in the amino acid sequence corresponding to SEQ ID NO: 2 or 4 of the nitrate reductase protein from proline to an amino acid residue other than proline.

In one embodiment, the present invention may be a tobacco plant obtained by crossbreeding a tobacco plant in which the amino acid residue corresponding to position 525 in the amino acid sequence corresponding to SEQ ID NO: 2 or 4 is mutated from proline to an amino acid residue other than proline with a tobacco plant in which the nitric acid content and/or TSNA is reduced by a mechanism different from the tobacco plant of the present invention, and the posterity thereof. Examples of such a crossbreeding parent include a mutant that is modified so that CYP82E4, which is a main nicotine demethylase, does not function and a mutant of a nitric acid transporter.

In Example herein, a tobacco plant containing nitrate reductase in which an amino acid residue corresponding to position 525 in an amino acid sequence corresponding to SEQ ID NO: 2 or 4 was mutated from proline to leucin or serine was obtained. The nucleotide sequence mutation for changing the amino acid from proline to leucin was CCA→CTA, the nucleotide sequence mutation for changing the amino acid from proline to serine was CCA→TCA, and both are mutations of only one base.

Three bases substitution, TCA→GAT, is necessary for changing the amino acid from serine to aspartic acid at position 523 to obtain the nitrate reductase S523D, described in NPLs 2 and 3. The fact that the three bases need to be substituted means that it is very difficult to acquire a S523D mutant by modifying an endogenous nitrate reductase gene by mutation using a chemical or the like. Meanwhile, a tobacco plant containing the nitrate reductase in which the amino acid residue corresponding to position 525 in the amino acid sequence corresponding to SEQ ID NO: 2 or 4 is mutated from proline to leucin or serine is also easily acquired by mutation. Mutants are effective in business in view of the cultivation of recombinant crops being difficult institutionally in countries including Europe.

In nitrate reductase, a low conservative region connecting between conservative domains (hinge 1 region) is known. S523D, described in NPLs 2 and 3, exists in this hinge 1 region. In the present invention, when 26 tobacco plants having nitrate reductases in which an amino acid was mutated in the hinge 1 region were obtained, and the amount of nitric acid in leaves thereof were examined, it was in only two P525 mutants of the present invention that the decrease was seen.

4. Leaf Tobacco and Cured Leaves

In one embodiment, the present invention relates to leaf tobacco harvested from the tobacco plant of the present invention. The present invention also relates to cured leaves generated from the leaf tobacco of the present invention.

The meaning of the "tobacco leaves of the present invention" is as described in "3. Method for producing tobacco plant" and the part previous thereto.

The step of producing cured leaves from leaf tobacco is not particularly limited, and can be performed using a well-known method. The leaves of the tobacco plant are harvested, and can be used as a material for producing tobacco products and the like. The tobacco leaves may be air-cured, fire-cured, flue-cured, or open air-cured. Unlimitedly, the air curing is curing the tobacco leaves for 4 to 8 weeks by exposing tobacco leaves to air with the tobacco leaves hung in a well-ventilated shed. The fire cured tobacco is obtained by heat-curing the tobacco leaves by fire continuously or intermittently for 3 days to 10 weeks depending on the step and tobacco with the tobacco leaves hung in a large shed. The flue-cured tobacco is obtained by usually curing the tobacco leaves with tobacco hung in a row in a curing hut and the temperature raised slowly over 1 week. The open air curing-treated tobacco is obtained by curing in the sun. This method is used to produce oriental leaf tobacco in Turkey, Greece, and other Mediterranean countries.

In one embodiment, the present invention relates to cured leaves derived from leaf tobacco of the present invention and cured leaves of the leaf tobacco.

In one embodiment, the leaf tobacco and the cured leaves contain a nitrate reductase protein in which an amino acid residue corresponding to position 525 in an amino acid sequence corresponding to SEQ ID NO: 2 or 4 is mutated from proline to an amino acid residue other than proline or a nucleic acid encoding the protein.

In one embodiment, the cured leaves decease in tobacco-specific nitrosamines (TSNAs) as compared with cured leaves generated from the leaf tobacco of the tobacco plant that is described in "2. Properties of tobacco plant", and is a control.

Four components of TSNA
N-Nitrosonornicotine (NNN)
N-Nitrosoanatabine (NAT)
N-Nitrosoanabasine (NAB)
Nicotine-derived nitrosoketone (NNK)

In Example 7, the homozygotes of P525L and P525S decreased in the total of the four components (NNN, NAT, NAB, and NNK) of TSNA by 34 to 36% as compared with cured leaves generated from the leaf tobacco of the tobacco plant that was a control. In one embodiment, the tobacco plant decreases in at least one component of TSNA or the total of TSNA by at least 5%, 10%, 15%, 20%, 25%, or 30% as compared with the control.

5. Cut Filler, Powder, Sheet, Stem, Granules, Extract, and Composition

In one embodiment, the present invention relates to a cut filler, powder, a sheet, a stem, granules or an extract produced from cured leaves of the present invention.

The meaning of the "cured leaves of the present invention" is as described in "4. leaf tobacco and cured leaves" and the part previous thereto.

The "cut filler" is a substance obtained by shredding cured tobacco leaves in a long and narrow strip shape, and is used for cigarettes.

The "stem" is the thickest leaf vein portion running at the center of a leaf.

The "powder" is a substance obtained by ground cured tobacco leaves into a powdery shape.

The "granule" is a substance obtained by forming powder into a granular shape.

The "extract" is a substance obtained by extracting a component from a material such as leaves or stems ("portions", preferably including "non-proliferative portions") derived from the tobacco plant for improving the flavor of the tobacco product or reducing the content of a specific component in the tobacco product. As the extracting method, a well-known method for extracting essential oil, a specific component, or the like from a plant can be used.

The present invention unlimitedly relates to a composition containing a tobacco plant (including portions) or cured leaves, or tobacco materials derived from these (cut filler and the like) of the present invention. The composition obtained without doing anything about a tobacco plant or a portion thereof, or by cutting, ground, or milling a tobacco plant into a small piece shape, a slurry shape, or a fine powder shape may be used. As the composition, a tobacco plant or a portion thereof harvested from farmland or the like may be used as it is, a tobacco plant or a portion thereof obtained by partially evaporating water therefrom inside or outside for a predetermined period may be used, or a tobacco plant or a portion thereof obtained by evaporating most of water therefrom with a dryer or the like may be used.

The composition may unlimitedly contain a cut filler, powder, a sheet, a stem, granules, or an extract produced from cured leaves of the present invention.

In one embodiment, the cut filler, the powder, the sheet, the stem, the granules, or the extract, and the composition of the present invention contain non-proliferative portions of the tobacco plant.

In one embodiment, the cut filler, the powder, the sheet, the stem, the granules, or the extract, and the composition of the present invention contain a nucleic acid encoding nitrate reductase in which an amino acid residue corresponding to position 525 in an amino acid sequence corresponding to SEQ ID NO: 2 or 4 is mutated from proline to an amino acid residue other than proline.

6. Product

In one embodiment, the present invention relates to a tobacco product containing cured leaves of the present invention, and/or the cut filler, the powder, the sheet, the stem, the granules, or the extract of the present invention.

The meaning of the "cured leaves of the present invention, and/or the cut filler, the powder, the sheet, the stem, the granules, or the extract of the present invention" is as described in "5. Cut filler, powder, sheet, stem, granules, extract, and composition" and the part previous thereto.

The type of the "tobacco product" is not particularly limited. Cigars, pipe tobacco, snuff tobacco (including snus and snuff), chewing tobacco, divided tobacco (including fine cut), hookah, and the like are included besides cigarettes. Furthermore, non-combustion heated tobacco products, wherein aerosol generated by heating the tobacco is used as an aerosol source, unheated tobacco products, wherein the flavor thereof is aspirated without heating the tobacco, and the like are included.

The "tobacco product" unlimitedly includes non-proliferative portions of the tobacco plant.

In one embodiment, the present invention provides the use of the tobacco plant, the leaf tobacco, and the cured leaves of the present invention for producing the tobacco product.

In one embodiment, the present invention relates to the use of the tobacco plant, the leaf tobacco, and the cured leaves of the present invention as the tobacco product.

In one embodiment, the present invention relates to the tobacco product of the tobacco plant, the leaf tobacco, and the cured leaves of the present invention to be used as the tobacco product.

In one embodiment, the present invention includes a method for producing the tobacco product. The method for producing the tobacco product unlimitedly includes preparing a material derived from a tobacco plant from the modified tobacco plant containing the nitrate reductase in which an amino acid residue corresponding to position 525 in the amino acid sequence corresponding to SEQ ID NO: 2 or 4 is mutated from proline to an amino acid residue other than proline. The production method may include a step of collecting leaves from the tobacco plant to prepare cured leaves. As the method for producing the tobacco product, a well-known method can be used. For example, the tobacco product can be produced from leaves collected from the modified tobacco plant (leaf tobacco) through a raw material step (rating, vein removal, adjustment, curing, storage, and aging), a raw material processing step (sheet, extraction, granules, heating, and casing), and a product step (blend, shredding, rolling, and packing).

The definition of the "tobacco product" is as described above.

EXAMPLES

Hereinafter, the present invention will be described in detail based on the Examples, but the present invention is not limited to these Examples. Those skilled in the art can easily add modification and mutation to the present invention based on the description of the present specification, and they are included in the technical scope of the present invention.

Comparative Example 1 Production of Recombinants Constitutively Expressing S523D and WT In the present Comparative Example, recombinants constitutively expressing S523D and WT were produced.

(1) Vector Construction

The artificially synthesized DNAs of ORF in which mutation was introduced so that serine (S) at position 523 of an NIA2 polypeptide (SEQ ID NO: 4) was changed into aspartic acid (D) (S523D) and the ORF of wild type NIA2 (WT) were purchased from Genewiz. CAT was added to the 5'-termini, and GTCGAC was added to the 3'-termini so that NdeI and SalI can cleave the 5'-termini and the 3'-termini, respectively. TTC at positions 1869 to 71 of the ORF of the wild type NIA2 (SEQ ID NO: 3) was substituted with AAG for distinction from the endogenous NIA2 without causing amino acid substitution mutation (equivalent to base 1872 to 74 of SEQ ID NO: 25), and a HindIII site was introduced. The nucleotide sequence of the synthetic DNA encoding NIA2 S523D is represented by SEQ ID NO: 24, and the nucleotide sequence of the synthetic DNA encoding wild type NIA2 is represented by SEQ ID NO: 25.

The NdeI/SalI digested fragments of the above-mentioned DNAs were introduced into pRI201-AN (Takara Bio Inc.), having the 35S promoter. The sequences of the whole insertions including the sites bound to the vectors were confirmed using primers for sequencing (Table 1).

TABLE 1

| Primer name | Sequence |
|---|---|
| Nia2_ex1_2F | ACCGAAGCATGGTGGTACAA (SEQ ID NO: 9) |
| Nia2_ex2_3F | GGCTATTCTTATTCTGGCGGAG (SEQ ID NO: 10) |
| Nia2_ex3_4R | CATCATTCCCATGACGTTCC (SEQ ID NO: 11) |
| Nia2_ex4_HindIII_R | GCTGCTGAAGCTTGAAGATCC (SEQ ID NO: 12) |

Agrobacteria (*Agrobacterium tumefaciens* LBA4404) were transformed by electroporation with the plasmids the sequences of which were confirmed, and were used for transforming tobacco.

(2) Tobacco Transformation

A tobacco (cultivar: Petit Havana SR-1) was transformed individually with Agrobacteria having the two constructs produced in (1). Individuals the rooting of which was confirmed were analyzed for the introduced gene expression in leaves of the shoots. Individuals in which introduced gene expression was confirmed by the method described in the following "(3) Confirmation of introduced gene expression" was transplanted into No. 3 pots filled with fertile soil. These individuals at T0 generation were cultivated in a gene-recombination greenhouse to gather self-pollination T 1 seeds.

(3) Confirmation of Introduced Gene Expression

RNA was extracted from the leaves using an RNeasy Plant Mini Kit (QIAGEN K.K.), cDNAs were synthesized using a PrimeScript™ RT reagent Kit with gDNA Eraser (Takara Bio Inc.), and the levels of expression derived from the introduced mutated NIA2 cDNAs were analyzed using Taq Man Fast Advanced Master Mix (Thermo Fisher Scientific K.K.) and Step OnePlus Real-Time PCR Systems (Thermo Fisher Scientific K.K.).

The primer and probe sequences are as described in Table 2. The relative levels of the expression (dCt) with respective to that of the control was compared using the elongation factor-1α gene (Accession No. AF120093, elf) as a control.

TABLE 2

| Primer/probe name | | Sequence |
|---|---|---|
| NRs_TMF | Primer | CAGGATTGGTGAACTCATAACTAC (SEQ ID NO: 13) |
| NRs_TMR | Primer | CTCTGCGCTGGAACAAGT (SEQ ID NO: 14) |
| NRs_wt_WGB | Probe | GATCTTCTTCCTTCAGCAGC (SEQ ID NO: 15) |
| NRs_tg_MGB | Probe | GGATCTTCAAGCTTCAGCAG (SEQ ID NO: 16) |
| elfa_v2_TMF | Primer | CTAAGGGTGCTGCCAGCTTT (SEQ ID NO: 17) |
| elfa_v2_TMR | Primer | GTCAAGCACTGGAGCATATCCA (SEQ ID NO: 18) |
| elfa_v2_TMP | Probe | ATCATGAACCATCCAGGACAGATTGG (SEQ ID NO: 19) |

Comparative Example 2 Analysis of Recombinants Constitutively Expressing S523D and WT In the present Comparative Example, recombinants constitutively expressing S523D and WT, and were acquired in Comparative Example 1 were analyzed. At the T1 generation, the introduced gene expression was also confirmed in the method described in Comparative Example 1 (3), and the following tests were performed.

(1) Liquid Fertilizer Cultivation

T1 seeds of Comparative Example 1 (2) were sown and temporarily planted around 2 weeks after, and the seedlings around 2 weeks after the temporary planting were transplanted into No. 4 pots. The temporarily planted seedlings were moved together with fertile soil, and around 400 ml of vermiculite was packed. Nitric acid liquid fertilizer (20 mM as $NO_3$: 4 mM $Ca(NO_3)_2$, 4 mM $Mg(NO_3)_2$, 4 mM $KNO_3$) was fed, and cultivation was performed in a Koitotoron under the conditions of 25° C. in the light period/18° C. in the dark period, a day length of 12 hours, and a humidity of 60%. The cultivation was performed at a luminosity of 10000 luxes to 15000 luxes in the light period and performed under the shading conditions with all the lamps in the Koitotoron off in the dark period.

(2) Nitric Acid Quantification

Leaves (3 to 8) were collected, and the laminas from which stems were removed were cured at 80° C. for one night or longer. To these dry powders was added 1 ml of MQ water per 100 mg of dry powder, and the mixture was shaken and extracted for 1 hour or more. The filtrate was measured as a measurement sample for nitric acid using a Nitrachek 404 Meter (KPG Products Ltd.) according to the attached manual.

It was confirmed that, as reported previously (for example, PTL 1 and NPL 2), the amount of nitric acid in the leaves (laminas) decreased dramatically due to the constitutive expression of NIA2 having S523D mutation (NIA2_S523D) (FIG. 1). Meanwhile, a decrease in the amount of nitric acid by around ½ to ¼ also due to the constitutive expression of wild type NIA2 (NIA2_WT) was seen as compared with the control not constitutively expressing NIA2 (FIG. 1).

Figure 2:
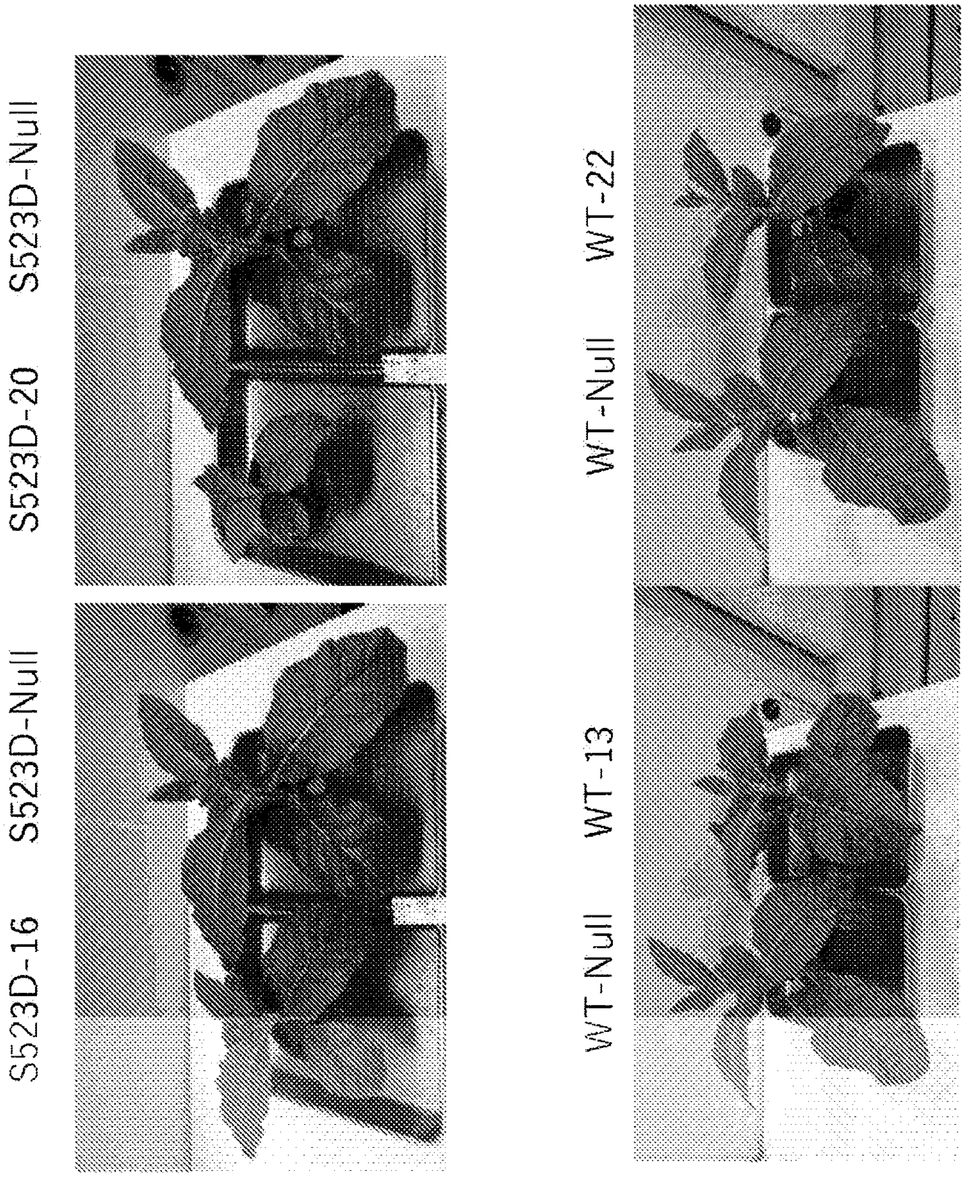
FIG. 2 is photographs of plant bodies around 3 weeks after transplantation. S523D-16: plant body constitutively expressing NIA2 having S523D mutation (NIA2_S523D), T1 generation; S523D-20: plant body constitutively expressing NIA2 having S523D mutation (NIA2_S523D), T1 generation; WT-13: plant body constitutively expressing wild type NIA2 (NIA2_WT), T1 generation; WT-22: plant body constitutively expressing wild type NIA2 (NIA2_WT), T1 generation; S523D-Null and WT-Null: plant bodies that express neither NIA2 S523D nor NIA2_WT, T1 generation

Although a great difference in vegetation was not seen regardless of the presence or absence of the constitutive expression in NIA2_WT, dwarfism, in which the size of the individual decreased, was exhibited due to the constitutive expression of NIA2_S523D (FIG. 2). This dwarf trait was observed from the early period of the vegetation (FIG. 3).

(3) Nitrous Acid Quantification

50 μl of a color reagent 1 (2% sulfanilamide in 3 N HCl) was mixed with 100 μl of a sample, and the mixture was reacted at room temperature for 5 minutes. 50 μl of a color reagent 2 (0.1% N-naphthyl ethylenediamine in water) was added/mixed, and the mixture was reacted at room temperature for 10 minutes. A540 and A700 as a control were measured with the microplate reader Infinite 200 PRO (Tecan Japan Co., Ltd.), and A540-A700 (difference) was defined as a measured value. 100 μl of $NaNO_2$ (FUJIFILM Wako Pure Chemical Corporation, special grade) was also measured for an analytical curve in the same way, the analytical curve was drawn, and the amount of nitrous acid was calculated.

(4) Dark Place Nitrous Acid Elution Test

A dark place nitrous acid elution test was performed with reference to the method of Lea et al. (NPL 4). Leaf discs of NIA2_S523D were immersed in an elution buffer (50 mM Hepes-NaOH pH7, 50 mM $KNO_3$), shaded from light with aluminum foil, and shaken and reacted under the conditions of 28° C. and 100 rpm for 5 hours. The elution buffer was collected, and nitrous acid was quantified in the method described in "(3) Nitrous acid quantification". 200 μl of the elution buffer per leaf disc having a diameter of 4 mm was used.

SR-1, which was the control, the recombinant constitutively expressing NIA2_S523D, and the recombinant constitutively expressing NIA2_WT were transplanted into No. 4 pots. Five leaf discs (4 mm in diameter) were collected from a tobacco subjected to liquid fertilizer cultivation for 10 days, weighed, and then immersed in 1 ml of the elution buffer. Nitrous acid eluted in the elution buffer was expressed in an amount per raw leaf weight.

Figure 4:
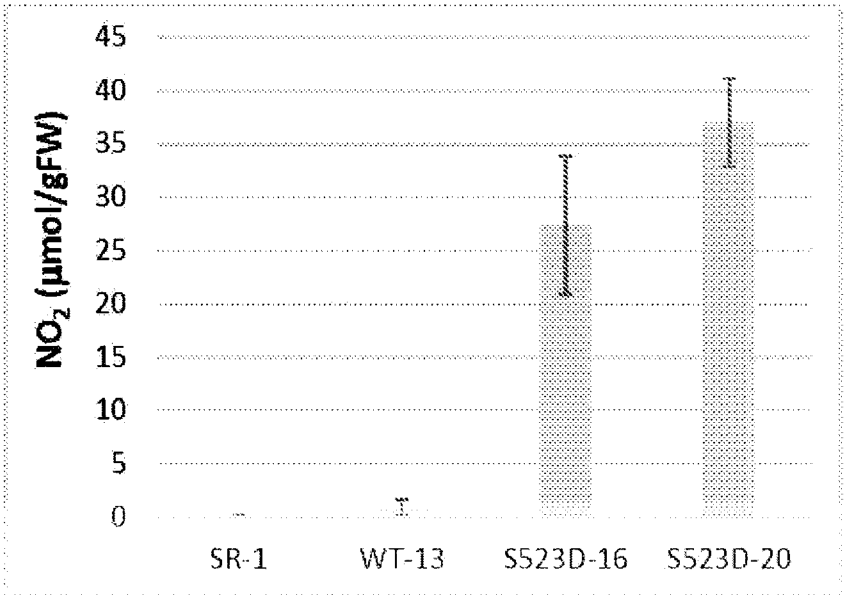
FIG. 4 is results of a dark place nitrous acid elution test of recombinants constitutively expressing NIA2_S523D, recombinants constitutively expressing wild type SR-1, and a recombinant constitutively expressing NIA2_WT (WT-13). S523D-16 and S523D-20 are two different lines of T1 generation derived from different TO individuals. The number of replications is 4, and error bars indicate standard deviations.

While the elution of nitrous acid in the dark place was hardly seen in SR-1 and the recombinant constitutively expressing NIA2_WT, which were wild types, marked elution was seen in the recombinant constitutively expressing NIA2_S523D (FIG. 4).

(5) NR Enzyme Activity

The plants temporarily planted in (1) were placed under the light condition (L) or the dark condition (D). The room temperature was adjusted to 25° C., and the humidity was adjusted to 60% under both the light condition and the dark condition. Under the light condition, the luminosity was adjusted to 10000 luxes to 15000 luxes, and under the dark condition, shading was performed with all the lamps in Koitotoron off. After 2 hours, around 0.1 g of leaves (laminas) were collected in a 2-ml tube and promptly frozen in liquid nitrogen. The collected leaf tissues were freeze-fractured (1000 rpm, 30 seconds, twice) with a Shake Master Neo (bio medical science). An extraction buffer (final concentration; 0.1 M Hepes pH7.5, 10 mM $MgCl_2$, 3% PVP, 1× cOmplete™, EDTA-free (Roche Diagnostics K.K.), 2 mM DTT) having a volume that is 8 times the volume thereof was added to the freeze-fractured tissues, and the mixtures were well mingled and placed on ice. Centrifugation (6000 rpm, 4° C., 15 minutes) was performed, and the supernatant (crude extract liquid) was collected in 1.5-ml tubes. Then, portions of the mixtures were poured into other 1.5-ml tubes and 5 times diluted with ultrapure water. In some cases, $MgCl_2$ at a final concentration of 10 mM or EDTA at a final concentration of 10 mM was added to the extraction buffer to prepare crude extract liquids.

The activity was measured as follows. 20 μl of the 5 times diluted crude extract liquid was added to 80 μl of an activity measurement buffer (final concentration; 50 mM Hepes pH 7.5, 10 mM $KNO_3$, 10 mM $MgCl_2$, 5 μM FAD, 0.15 mM NADH), and the mixture was reacted (30° C., 60 minutes). The reaction was performed by two methods in which $MgCl_2$ at a final concentration of 10 mM or EDTA at a final concentration of 10 mM was added to the activity measurement buffer with respective to one crude extract liquid. The amount of nitrous acid generated in the reaction liquid was measured according to the method for quantifying nitrous acid described in "(3) Nitrous acid quantification". The ratio between the values measured by the two above-mentioned methods was calculated, and the activity of the nitrate reductase (NR activation rate) was obtained.

Figure 5:
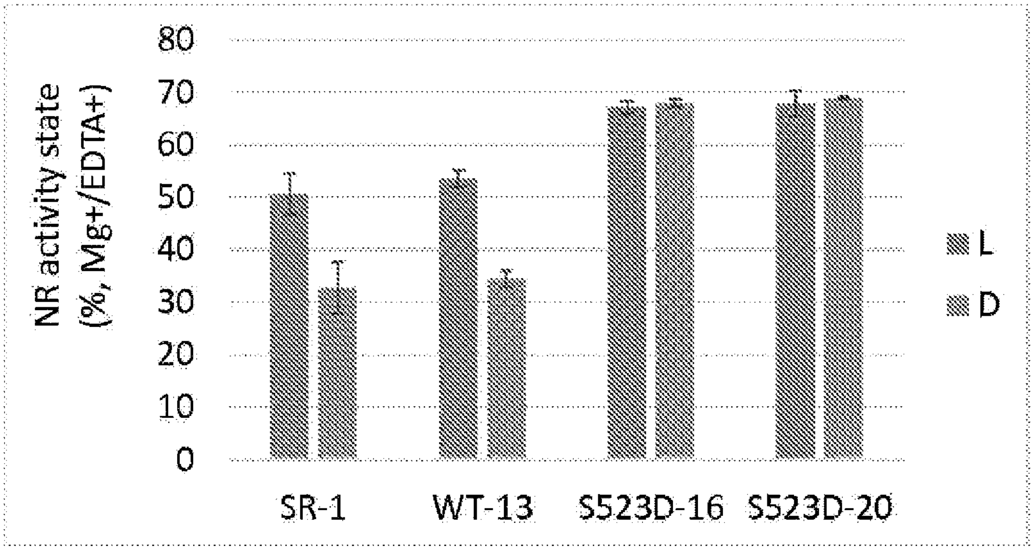
FIG. 5 is results of the analysis of the activation rates in a test on the nitrate reductase activities (NR activities) under the light condition (L) (left) and the dark condition (D) (right) of recombinants constitutively expressing NIA2 S523D and recombinants constitutively expressing wild type SR-1 and recombinants constitutively expressing NIA2 WT (WT-13). S523D-16 and S523D-20 are two different lines of T1 generation derived from different TO individuals. The number of replications is 4, and error bars indicate standard errors.

While, in SR-1 and the recombinant constitutively expressing NIA2_WT, which were wild types, the NR activation rates under the dark condition (D) was clearly low as compared with the light condition (L), a decrease in the NR activation rate under the dark condition was not seen in the recombinant constitutively expressing NIA2_S523D (FIG. 5).

Example 1 Production and Selection of Ethyl Methanesulfonate (EMS) Mutants

In the example, ethyl methanesulfonate (EMS) mutants of a tobacco plant were produced.

(1) Mutation Introduction by EMS Treatment

Seeds of tobacco (variety: Tsukuba1) were treated with ethyl methanesulfonate (EMS) to produce mutant panels (TUMs) (Heisei 23-nen Nihonshokubutsubyorigakkai Taikai P234, Tabako Henitai Paneru no Sakushutsu (The Convention of the Phytopathological Society of Japan in 2011 P258, Production of Tobacco Mutant Panel): NPL 5). Specifically, 200 mg of the seeds, 1 ml of water, and 6 to 8 μl of EMS (Sigma-Aldrich Co. LLC) were added to a 2-ml screw cap tube, well stirred and mixed by upsetting or the like, and the mixture was then shaken at room temperature and 60 rpm for 18 hours. The tube was centrifuged, the supernatant was removed, 1 ml of water was added, and shaking and washing were performed for 30 minutes. The centrifuged supernatant was removed, 1 ml of water was added, the tube was upset or the like, and the seeds were rinsed. This rinsing operation was repeated 3 times. This washing and rinsing operation was further repeated twice, and the seeds were dried on a filter paper. The dried seeds were cultivated in fertile soil, and M2 seeds obtained by self-pollination were gathered. Some of the M2 seeds were sown, and genomic DNAs were extracted from eight individuals of the young seedlings using a Gentra Puregene Tissue Kit (QIAGEN K.K.). The concentrations of the extracted genomic DNAs were adjusted to 10 ng/μl. The mutant panels include sets of these M2 seeds and the extracted bulk genomic DNAs.

(2) PCR

The hinge 1 region was amplified by PCR using the genomic DNAs of the mutant panels produced in "(1) Mutation introduction by EMS treatment" as templates.

The amplification was specifically performed using TKS Gflex DNA Polymerase (Takara Bio Inc.) according to the manual attached to the kit (95° C.; 1 minute, [98° C.; 10 seconds, 55° C.; 15 seconds, 68° C.; 1 minute]×35 to 40 cycles, 68° C.; 1 minute). The reaction time at 68° C. was increased or decreased to 1 minute per 1 kb according to the estimated size of the amplified fragment.

The following amplification primers of the hinge 1 region were used.

```
NIA1
NIA1_hinge1_F2
                                          (SEQ ID NO: 20)
(TTAGGTGAAATAACGCTCTTACAC)

NIA1_hinge1_R2
                                          (SEQ ID NO: 21)
(CCTAATTGGAGAGAATCAAGGTAT)

NIA2
NIA2_hinge1_F2
                                          (SEQ ID NO: 22)
(ATTGTGCTATGTTGCAATGTTCAG)

NIA2_hinge1_R1
                                          (SEQ ID NO: 23)
(GGAAGAAGATCCGTGCACG)
were used.
```

(3) Sequence Analysis

The DNAs to be used as the templates were reacted using a Big Dye Terminator v.3.1 cycle sequencing kit (Thermo Fisher Scientific K.K.) by the method attached to the kit (94° C. 30 seconds, 96° C. 10 seconds/50° C. 5 seconds/60° C. 2 minutes×25 cycles). Then, purification was performed using a BigDye XTerminator™ Purification Kit (Thermo Fisher Scientific K.K.) by the method attached to the kit. Sequence information was obtained with an Applied Biosystems® 3730 DNA Analyzer (Thermo Fisher Scientific K.K.) and analyzed with the sequence assembly software ATGC (GENETYX CORPORATION).

The primers for sequencing described in SEQ ID NOs: 20 and 22 were used.

(4) EMS Mutant

As a result of the sequence analysis in "(3) Sequence analysis", 26 lines of missense mutants having amino acid substitution in the hinge 1 regions of NIA1 and NIA2 in the M2 line obtained from the mutant panels were selected (Tables 3 and 4)

TABLE 3

| | NIA1 mutant line | Mutation |
|---|---|---|
| 1 | NIA1_C477Y | TGC ⇒ TAC |
| 2 | NIA1_E483K | GAG ⇒ AAG |
| 3 | NIA1_G485E | GGA ⇒ GAA |
| 4 | NIA1_P491S | CCG ⇒ TCG |
| 5 | NIA1_G495E | GGA ⇒ GAA |
| 6 | NIA1_G499S | GGT ⇒ AGT |
| 7 | NIA1_G499D | GGT ⇒ GAT |
| 8 | NIA1_E505K | GAG ⇒ AAG |
| 9 | NIA1_E509K | GAG ⇒ AAG |
| 10 | NIA1_A514T | GCA ⇒ ACA |
| 11 | NIA1_P515S | CCT ⇒ TCT |
| 12 | NIA1_P515L | CCT ⇒ CTT |
| 13 | NIA1_P525L | CCA ⇒ CTA |
| 14 | NIA1_P525S | CCA ⇒ TCA |
| 15 | NIA1_M527I | ATG ⇒ ATA |
| 16 | NIA1_S537L | TCG ⇒ TTG |

TABLE 4

| | NIA2 mutant line | Mutation |
|---|---|---|
| 1 | NIA2_M474I | ATG ⇒ ATA |
| 2 | NIA2_A503T | GCG ⇒ ACG |
| 3 | NIA2_H507Y | CAT ⇒ TAT |
| 4 | NIA2_E509K | GAG ⇒ AAG |
| 5 | NIA2_A512V | GCA ⇒ GTA |
| 6 | NIA2_E513K | GAG ⇒ AAG |
| 7 | NIA2_T524I | ACT ⇒ ATT |
| 8 | NIA2_N528K | AAC ⇒ AAA |
| 9 | NIA2_A530V | GCT ⇒ GTT |
| 10 | NIA2_A530T | GCT ⇒ ACT |

Example 2 Selection of Nitric Acid Decrease Lines

In the present Example, the M2 generation or the M3 generation of the EMS mutant lines selected in Example 1 was cultivated with liquid fertilizer, and it was analyzed whether nitric acid in tobacco leaves (laminas) decreased as compared with the control. The genomic DNAs were extracted from leaves of M2 and M3 individuals, and (2) PCR and (3) Sequence analysis of Example 1 were performed using them as templates, and mutated homozygotes and heterozygotes, and separated WT individuals, not including mutation, were selected.

Figure 6:
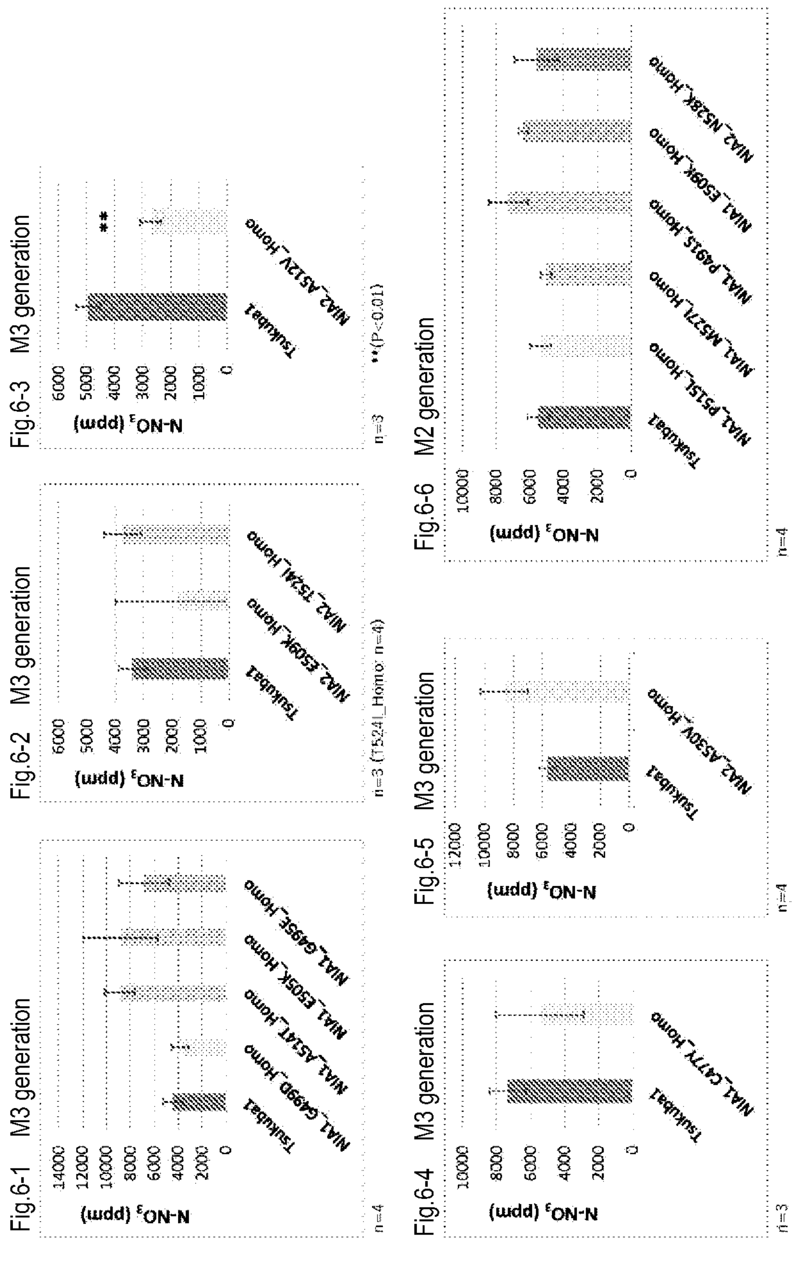
FIG. 6 is results of cultivating lines of M2 or M3 generation of EMS mutants having missense substitution mutation in the hinge 1 region of NIA1 or NIA2 and produced in Example 1 with liquid fertilizer to examine the amounts of nitric acid in tobacco leaves (laminas). Individuals having homozygous mutation were analyzed using the wild type tobacco Tsukuba1 as a control at the generations. The number of replications is 3 or 4, error bars indicate standard deviations.
Figure 7A:
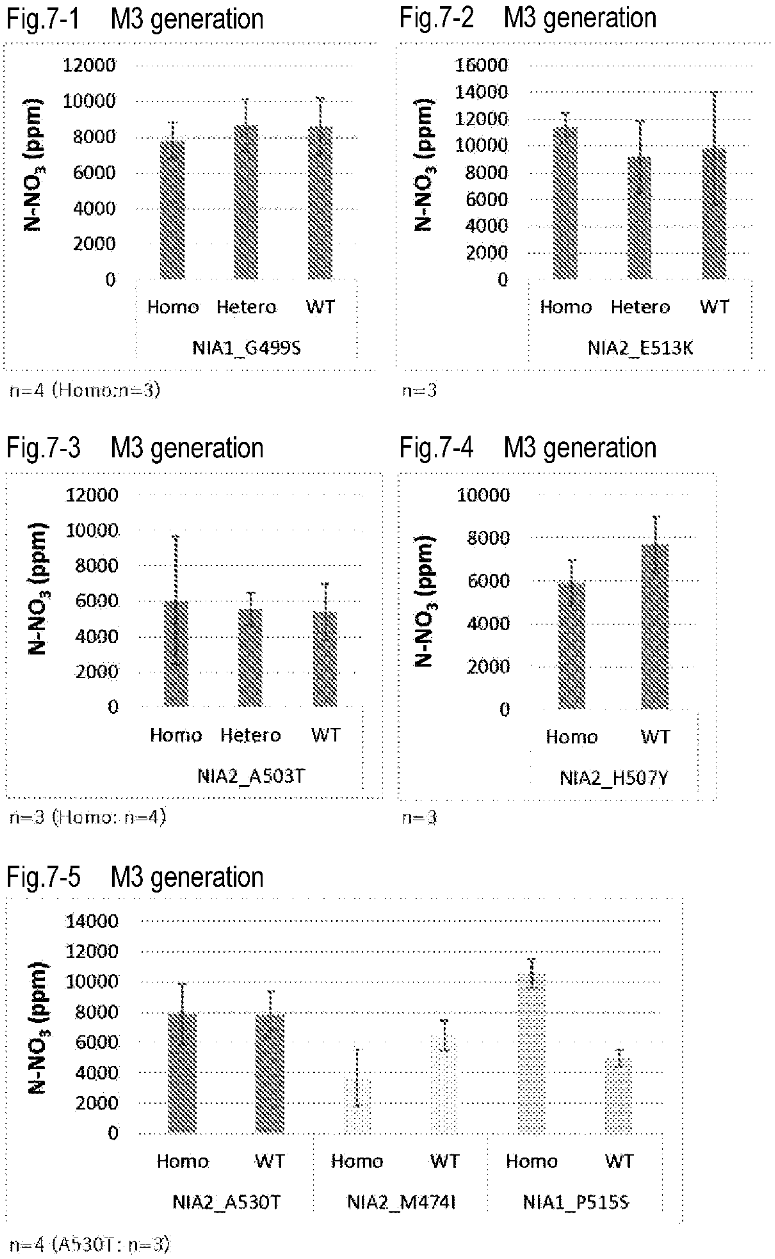
FIG. 7A is results of cultivating lines of M2 or M3 generation of EMS mutants having missense substitution mutation in the hinge 1 region of NIA1 or NIA2 and produced in Example 1 with liquid fertilizer to examine the amounts of nitric acid in tobacco leaves (laminas). Individuals having homozygous or heterozygous mutation were analyzed using WT individuals that have no mutation and in which the mutation is separated as controls at the generations. The number of replications is 3 or 4, error bards indicate standard deviations, and * indicates that there is a significant difference between the value and the control.
Figure 7B:
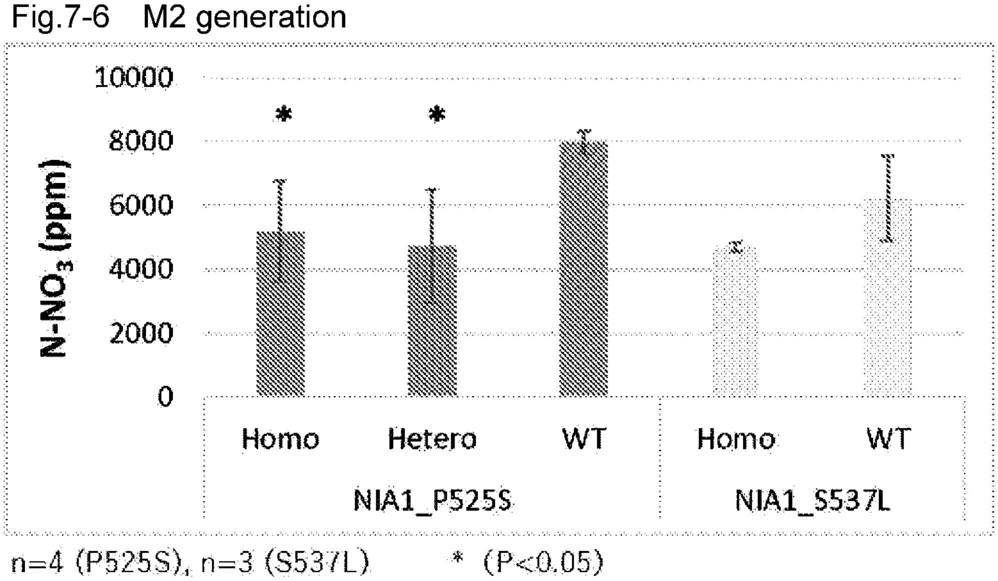
FIG. 7B is results of cultivating lines of M2 or M3 generation of EMS mutants having missense substitution mutation in the hinge 1 region of NIA1 or NIA2 and produced in Example 1 with liquid fertilizer to examine the amounts of nitric acid in tobacco leaves (laminas). Individuals having homozygous or heterozygous mutation were analyzed using WT individuals that have no mutation and in which the mutation is separated as controls at the generations. The number of replications is 3 or 4, error bars indicate standard deviations, and * indicates that there is a significant difference between the value and the control.
Figure 7B:
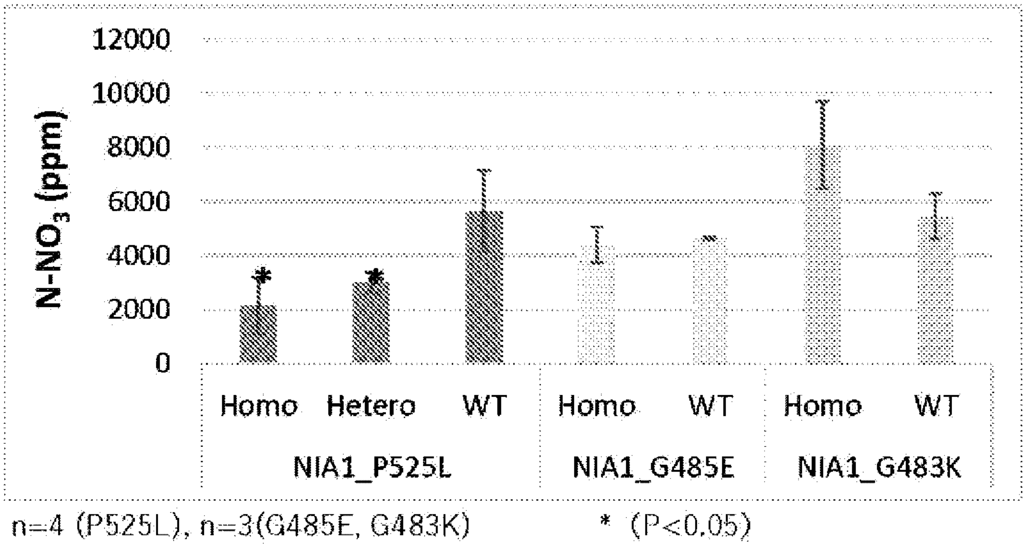
Figure 8:
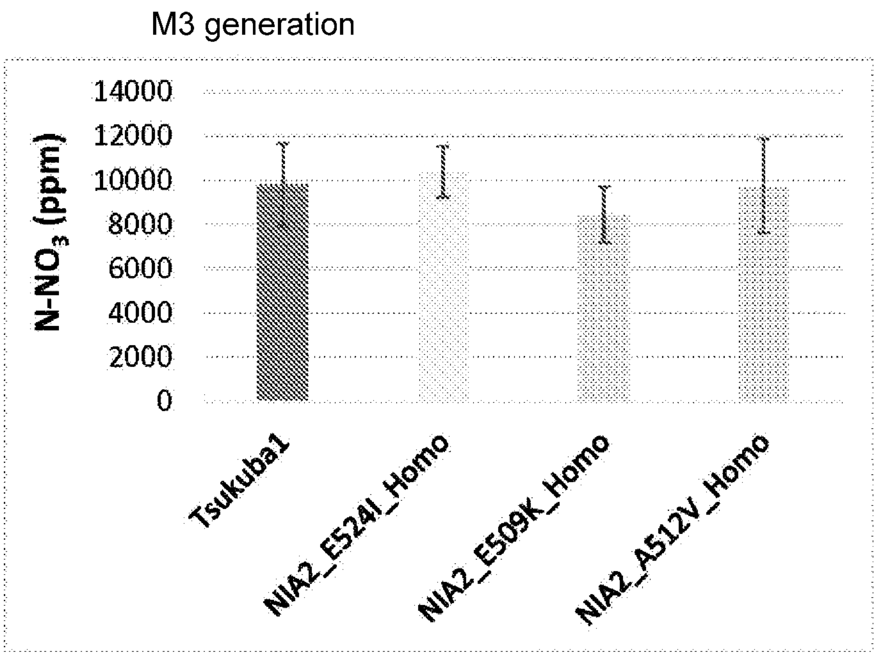
FIG. 8 is results of cultivating lines of M3 generation of EMS mutants having missense substitution mutation in the hinge 1 region of NIA2 and produced in Example 1 with liquid fertilizer to examine the amounts of nitric acid in tobacco leaves (laminas). Individuals having homozygous mutation were analyzed using the wild type tobacco Tsukuba1 as a control at the M3 generation. The number of replications is 4, and error bards indicate standard deviations.

The method for cultivating the tobacco plants and the method for quantifying nitric acid were performed in the same way as in "(1) Liquid fertilizer cultivation" and "(2) Nitric acid quantification" of Comparative Example 2. Sixteen lines of NIA1 mutants and 10 lines of NIA2 mutants having missense substitution mutations in the hinge 1 regions detected in Example 1 (Table 3) were targeted. Among 26 mutants, significant decrease in nitric acid was seen only in two lines that were NIA1_P525L and NIA1_P525S, in which substitution mutation was introduced into the amino acid at position 525 of the NIA1 gene (FIG. 6 to FIG. 8).

Example 3 Analysis of NR Activities of NIA1 P525L and NIA1 P525S

In the present Example, the NR activities of NIA1_P525L and NIA1_P525S were analyzed.

In Example 2, the activation rates of the NR enzyme activities of P525L and P525S, in which decrease in nitric acid in the laminas was confirmed, were analyzed under the light condition and the dark condition. The method was performed in the same way as in "(5) NR enzyme activity" of Comparative Example 2.

(1) Enzyme Activity

Figure 9:
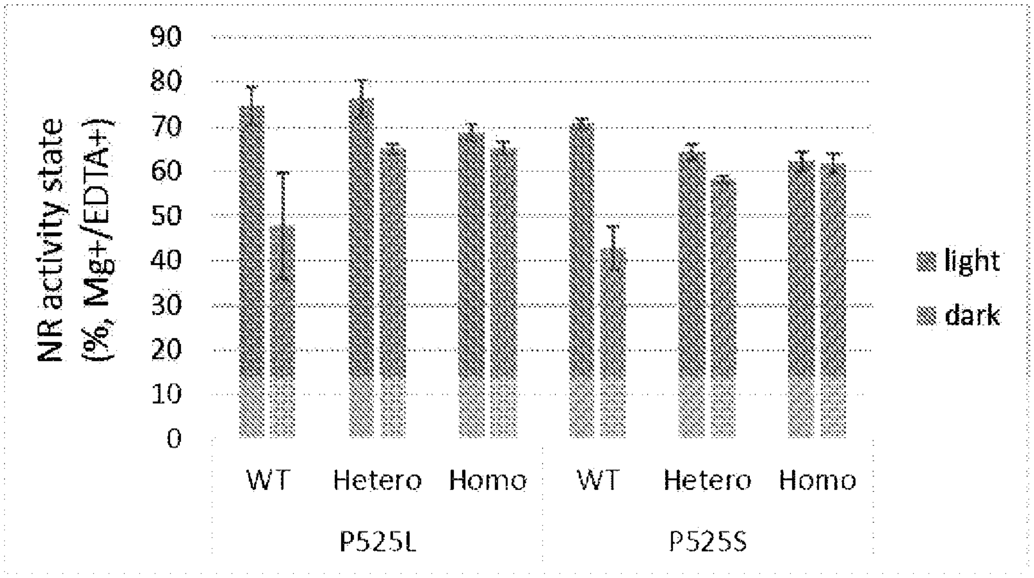
FIG. 9 is results of a test on the analysis of the activation rates under the light condition (light) (left) and the dark condition (dark) (right) of the nitrate reductase activity (NR activity) of NIA1 P525L and NIA1 P525S (M2 generation). Individuals having homozygous and heterozygous mutations were analyzed using WT individuals that have no mutation and in which the mutation is separated at the M2 generation as controls. The number of replications is 3 or 2, and error bars indicate standard errors.

The NR enzyme activation rate, obtained by expressing the NR activity value when Mg was added with respective to the NR activity value (NR maximum activity) when EDTA was added at the time of the activity measurement in percent (%), was analyzed. In both of the homozygotes and the heterozygotes of both mutation lines that were NIA1_P525L and NIA1_P525S, the NR activation rates were consequently as high even under the light condition as those under the dark condition (FIG. 9). Meanwhile, the NR activation rate under the dark condition of the separated WT (wild type), not having mutation, was markedly low as compared with under the light condition. It was considered from these results that since, in both mutants, the activities were not suppressed in the dark place, the amount of nitric acid accumulated decreased. The activation rates under the dark condition decreased slightly in not only the mutated homozygotes but also the mutated heterozygotes, and these results correspond with results of Example 2, in which decrease in nitric acid was seen even in the mutated heterozygotes (FIG. 7-6 and FIG. 7-7).

Example 4 Reconfirmation in M3 Generation of NIA1 P525L and NIA1 P525S

In the present Example, the nitric acid levels and the NR activities in the dark place of the M3 generation of NIA1_P525L and NIA1_P525S were analyzed.

The reconfirmation test was performed on the M3 generation of both mutated lines that were NIA1_P525L and NIA1_P525S, in which high NR activation rates and decrease in nitric acid in the dark place were confirmed in the M2 generation. The method was performed in the same way as in "(1) Liquid fertilizer cultivation", "(2) Nitric acid quantification", and "(4) Dark place nitrous acid elution test" of Comparative Example 2. In the dark place nitrous acid elution test, the amount of nitrous acid eluted per the number of leaf discs was however calculated.

(1) Dark Place Nitrous Acid Elution

Figure 10:
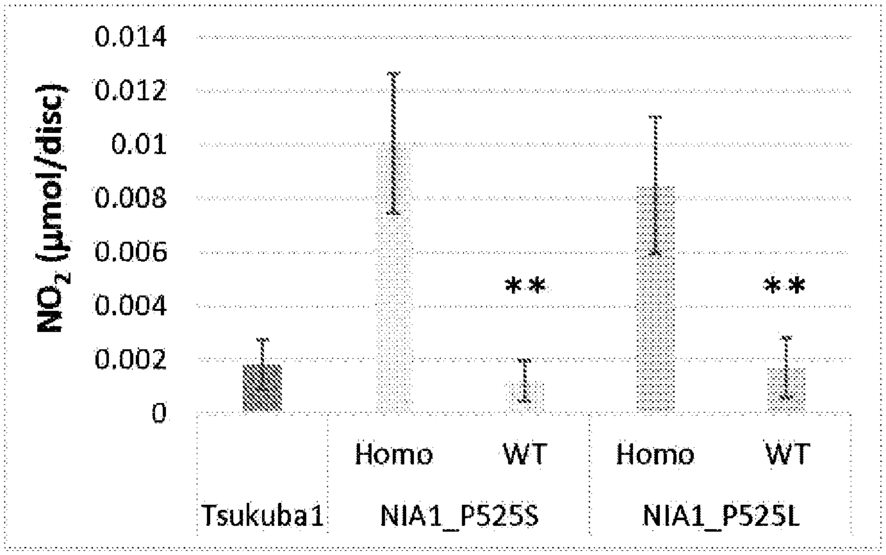
FIG. 10 is results of a dark place nitrous acid elution test of NIA1 P525L and NIA1 P525S (M3 generation). Individuals having homozygous mutation were analyzed using WT individuals that have no mutation and in which the mutation is separated at the M3 generation as controls. The number of replications is 4, error bards indicate standard deviations, and ** indicates that there is a significant difference between the value and the control.

In the homozygotes of both mutation lines that are NIA1_P525L and NIA1_P525S, marked nitrous acid elution was seen (FIG. 10). Meanwhile, the nitrous acid elution was hardly seen in the separated WT (not having P525 mutation) in the same way as the wild type Tsukuba1. It was reconfirmed from this that both of the mutated homozygotes of NIA1_P525L and NIA1_P525S had high NR activities in the dark place.

(2) Nitric Acid Quantification

Figure 11:
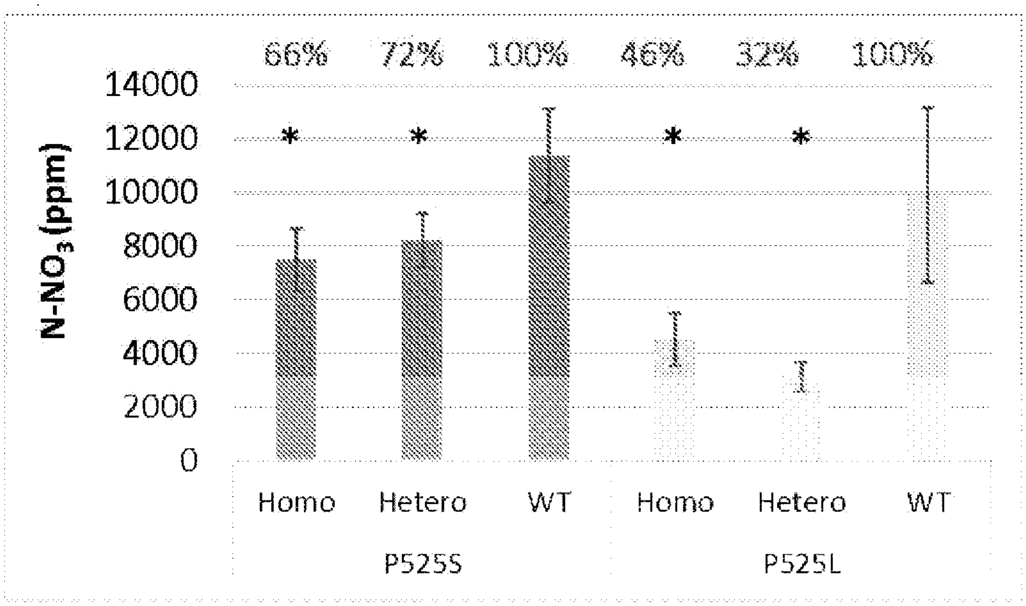
FIG. 11 is results of cultivating lines of M3 generation of NIA1_P525L and NIA1 P525S with liquid fertilizer to examine the amounts of nitric acid in tobacco leaves (laminas). Individuals having homozygous and heterozygous mutation were analyzed using WT individuals that have no mutation and in which the mutation is separated at the M3 generation as controls. The number of replications is 4, error bards indicate standard deviations, and * indicates that there is a significant difference between the value and the control.

In all of the homozygotes and heterozygotes of both mutated lines that were NIA1_P525L and NIA1_P525S, nitric acid decreased significantly as compared with in the separated WT individual (FIG. 11). The nitric acid level was 68% in NIA1_P525L, and was 34% in NIA1_P525S as compared with the control.

Figure 12:
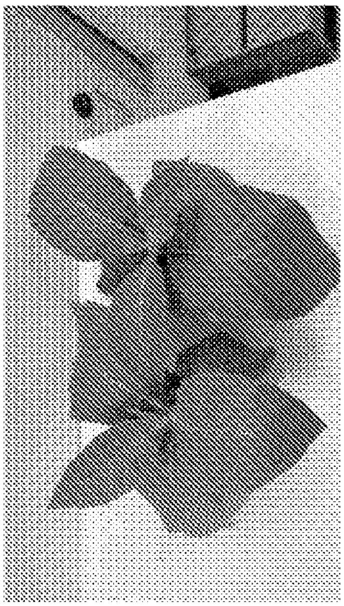
FIG. 12 is photographs of plant bodies of lines of M3 generation of NIA1 P525L and NIA1 P525S 16 days after transplantation. Individuals having homozygous and heterozygous mutation are shown using WT individuals that have no mutation and in which mutation is separated at M3 generation as controls.
Figure 12:
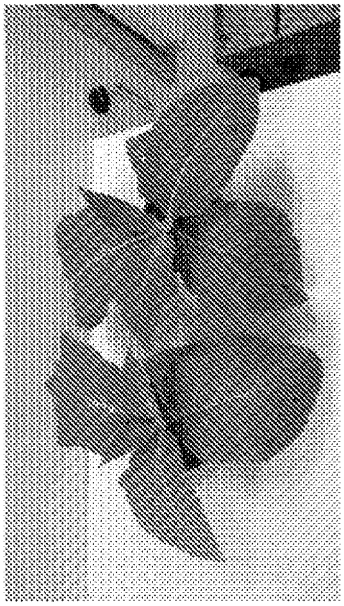
Figure 12:
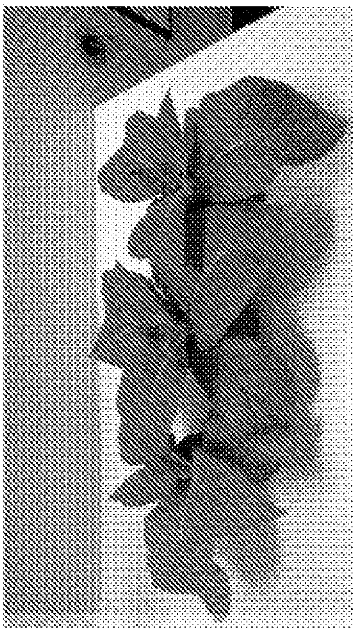
Figure 12:
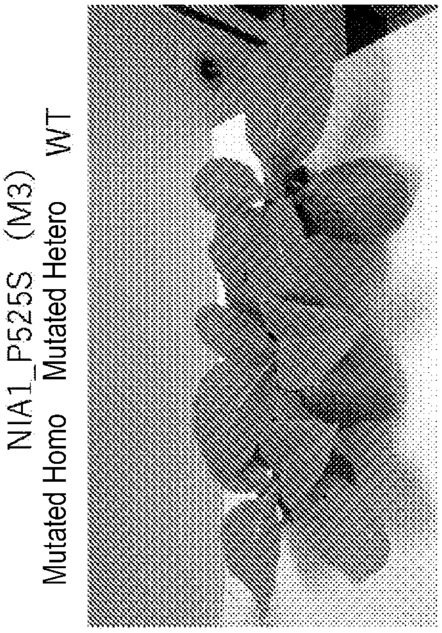

Abnormal vegetation was not seen in both mutated lines that were NIA1_P525L and NIA1_P525S regardless of the presence or absence of mutation unlike in the recombinant constitutively expressing NIA2_S523D (FIG. 12).

Example 5 Amount of Nitric Acid of Individuals of NIA1 P525L and NIA1 P525S Cultivated in Field In the present Example, NIA1_P525L and NIA1_P525S were examined for the amounts of nitric acid in individuals cultivated in a field.

A BC1F1 line was obtained by crossbreeding mutants having amino acid substitution mutations of P525L and P525S on the NIA1 gene with TN90 (Burley species). At BC1F2 generation obtained by the self-pollination of this, homozygotes and heterozygotes having the amino acid substitution mutation in NIA1 and the separated WT individuals, not including mutation, were cultivated in a field. Although the cultivation was performed by the standard method for farming the Burley species, 60% of the amount of base fertilizer was added between the ridges at the time of disbudding.

Three upper leaves 36 days after the disbudding were used as samples for analyzing nitric acid. Programed curing was performed using a thermo-hygrostat (ESPEC CORP.). The curing was performed under yellowing conditions (temperature: 38° C., relative humidity: 80% RH) for 5 days, browning conditions (temperature: 32° C., relative humidity: two upper leaves: 85% RH, one lower leaf: 90% RH) for 14 days, and stem curing conditions (temperature: 50° C., relative humidity: 40% RH) for 3 days. The laminas of the cured leaves were ground, and nitrate nitrogen was analyzed according to the instruction manual using an autoanalyzer QuAAtro 2 HR (BL TEC K.K.).

Figure 13:
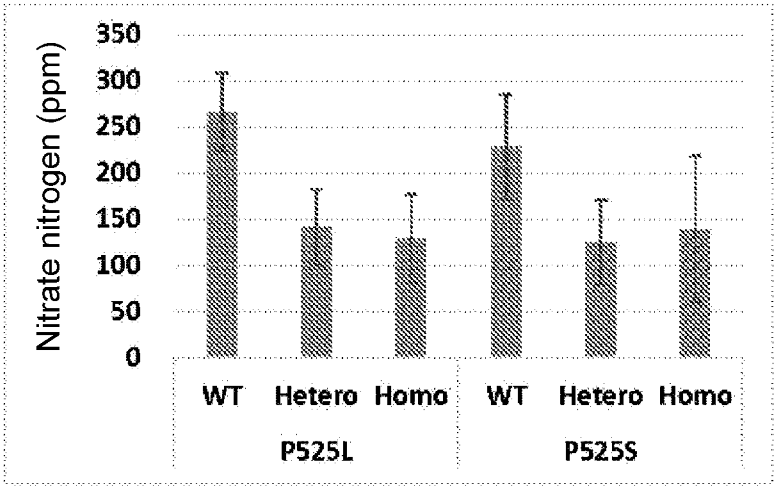
FIG. 13 is results of examining the nitrate nitrogen concentration in the cured leaves of homozygous or heterozygous individuals having P525L mutation and P525S mutation and WT individuals having no mutation as controls. The numbers of replications of WT, hetero, and homo of P525L are 6, 7, and 5, respectively, and the numbers of replications of WT, hetero, and homo of P525S are 4, 6, and 2 respectively. Error bars indicate standard errors (SEs).

The nitrate nitrogen concentration in the cured leaves of the homozygote or the heterozygote having P525L mutation was around ½ times that in the control (WT, not having mutation) (FIG. 13). The nitrate nitrogen concentration in the cured leaves of an individual having P525S mutation homozygously (homozygote) or heterozygously (heterozygote) was also around ½ times that in the control (WT, not having mutation) in the same way.

Example 6 Vegetation, Biomass, and Bloom of Recombinant Constitutively Expressing S523D and P525 Mutants In the present Example, the vegetation, biomass, and bloom of the recombinant constitutively expressing S523D and the P525 mutant were examined.

(1) Defective Vegetation of the Recombinant Constitutively Expressing S523D

TN90 (Burley species) was transformed, and T1 seeds were collected in the method described in "Comparative Example 1 Production of recombinants constitutively expressing S523D and WT (1) and (2)". Individuals highly expressing the introduced genes (S523D-OE and WT-OE) and individuals in which the expression was not seen (null segregants. S523D-null and WT-null) were selected at T1 generation and used for a test. Specifically, three lines of each recombinant (S523D-OE_1, 2, and 3 and S523D-null_1, 2, and 3) of T1 generation obtained by self-pollination the T0 generation into which NIA2_S523D was introduced, two lines of each recombinant (WT-OE_1 and 2 and WT-null_1 and 2) of T1 generation obtained by self-pollination the T0 generation into which NIA2_WT was introduced, and TN90, which was a host to be transformed, as the wild type were used for the test.

Figure 14:
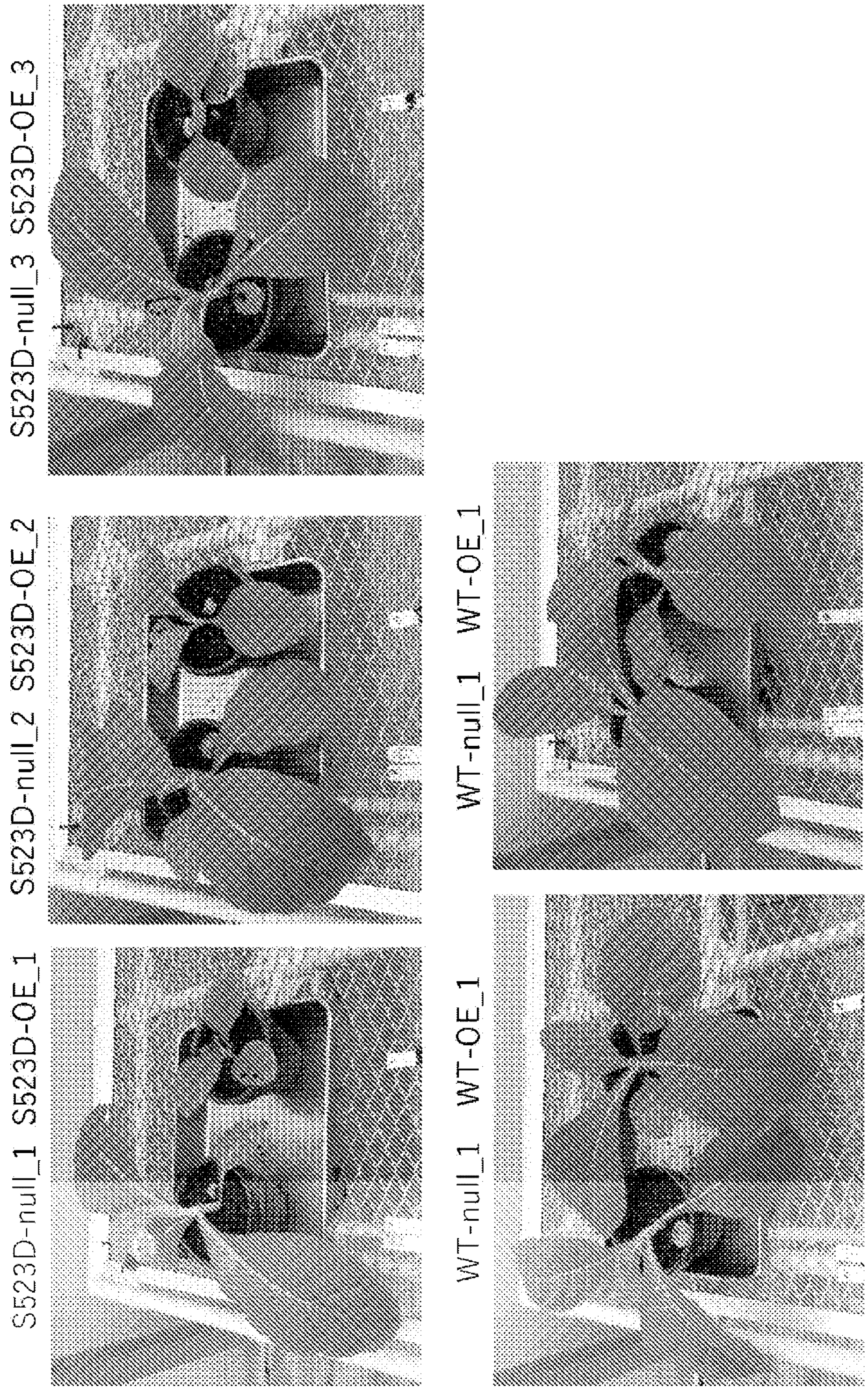
FIG. 14 is photographs of plant bodies of lines of T1 generation of S523D-OE, S523D-null, WT-OE, and WT-null of TN90 8 days after transplantation.

Individuals highly expressing the introduced genes (S523D-OE and WT-OE) and individuals not expressing the introduced genes (S523D-null and WT-null) were selected in the method described in "Comparative Example 1 Production of recombinants constitutively expressing S523D and WT (3)" using leaves of young plants cultivated in a closed greenhouse at 25° C. The selected individuals were transplanted into pots, and the cultivation was continued. Eight days after the transplantation, photographs of the individuals of the lines were recorded. All the three lines of T1 generation of S523D-OE, highly expressing NIA2_S523D, vegetated clearly and inferiorly as compared with S523D-null (FIG. 14). Meanwhile, marked difference in vegetation between the two lines of T 1 generation of WT-OE, highly expressing NIA2_WT, and the two lines of T1 generation of WT-null was not seen (FIG. 14).

Figure 15:
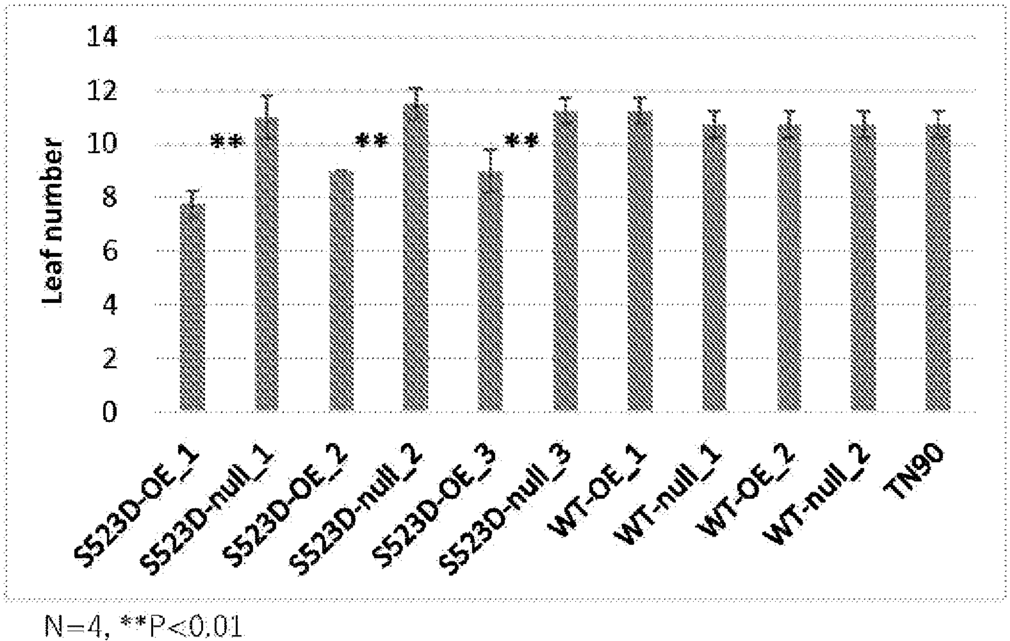
FIG. 15 is results of examining the numbers of leaves above the ground of lines of T1 generation of S523D-OE, S523D-null, WT-OE, and WT-null of TN90. The number of replications is 4, significant difference by the t-test: ** $P<0.01$, and error bars indicate standard deviations (SDs).
Figure 16:
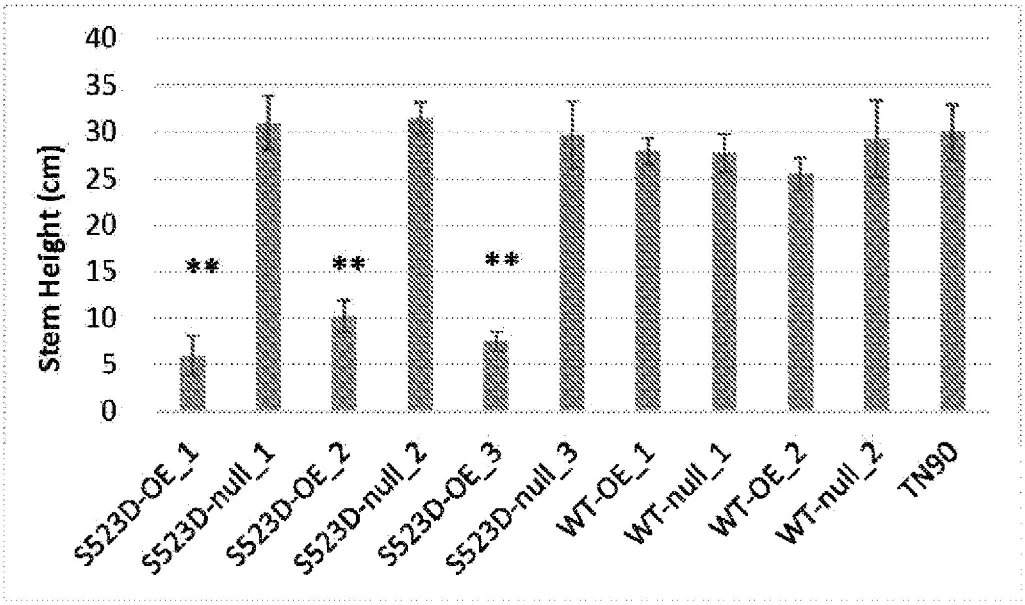
FIG. 16 is results of examining the stem heights of lines of T1 generation of S523D-OE, S523D-null, WT-OE, and WT-null of TN90. The number of replications is 4, significant difference by the t-test: ** $P<0.01$, and error bars indicate standard deviations (SDs).
Figure 17:
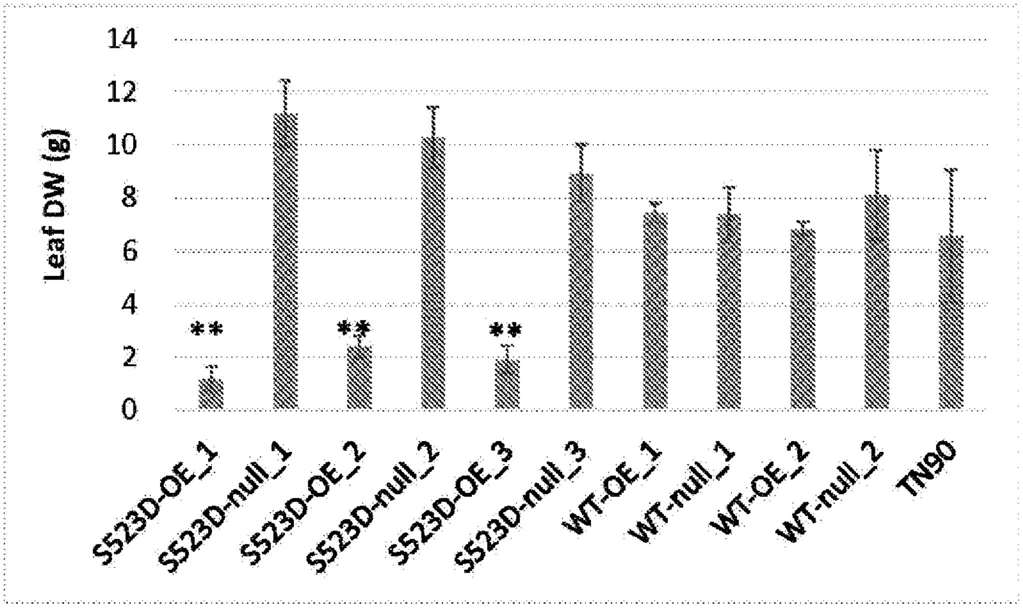
FIG. 17 is results of examining the dry matter weights of leaves above the ground (biomass) of lines of T1 generation of S523D-OE, S523D-null, WT-OE, and WT-null of TN90. The number of replications is 4, significant difference by the t-test: ** $P<0.01$, and error bars indicate standard deviations (SDs).

The defective vegetation specific to S523D-OE was already seen at the stage of the young seedlings. Four individuals of each line were measured for the number of leaves above the ground, stem height, the dry matter weight of leaves above the ground 23 days after the transplantation. Although the number of leaves above the ground of S523D-OE was 2 to 3 leaves fewer than that of S523D-null, a significant difference was not seen between WT-OE and WT-null (FIG. 15). The stem height and the dry matter weight (biomass) of leaves above the ground of S523D-OE were also markedly low as compared with S523D-null, and a significant difference was not seen between WT-OE and WT-null (FIG. 16 and FIG. 17).

The above showed that the high expression of NIA2_S523D caused marked defective vegetation in TN90 (Burley species). Since defective vegetation was not seen in WT-OE, it was considered that the defective vegetation was not influenced by the high expression of the NR protein itself but influenced by the high expression of the mutated NR protein the activity of which was not suppressed in the dark place (NIA2_S523D).

(2) Comparison Between Vegetation of Recombinant Constitutively Expressing S523D And Vegetation of P525 Mutants Transformants were produced with the knack described in (1) using Tsukuba1 (yellow species) as a host instead of TN90 and analyzed in the same way. Three lines of T1 generation obtained by self-pollination the T0 generation highly expressing NIA2_S523D were used for a test.

Individuals highly expressing the introduced gene (S523D-OE) and individuals not expressing the introduced gene (S523D-null) were selected using the leaves of the young plants cultivated in a closed greenhouse at 25° C. constantly and transplanted into pots, and the cultivation was continued. Two lines of each recombinant of the M3 generation having amino acid substitution mutation of P525L or P525S in NIA1 homozygously (homozygotes) were cultivated in the same way simultaneously. Three individuals of each line were measured for the number of leaves above the ground, the stem height, and the dry matter weight of leaves above the ground 34 days after the transplantation. With respective to three lines highly expressing S523D-OE and two lines of each of the homozygotes having the amino acid substitution mutations of P525L and P525S in NIA1, the results of a plurality of lines of each recombinant were collected and added together for comparison.

Figure 18:
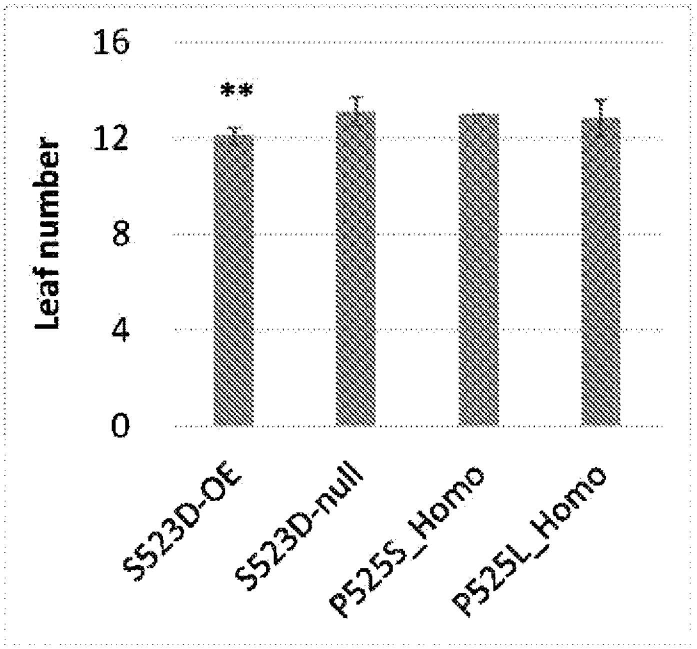
FIG. 18 is results of examining the numbers of leaves above the ground of lines of T1 generation of S523D-OE, S523D-null, P525L-Homo, and P525S-Homo of Tsukuba1. The number of replications is 9 (S523D-OE and Null) or 6 (P525S and P525L), significant difference by the t-test: ** $P<0.01$, and error bars indicate standard deviations (SDs).
Figure 19:
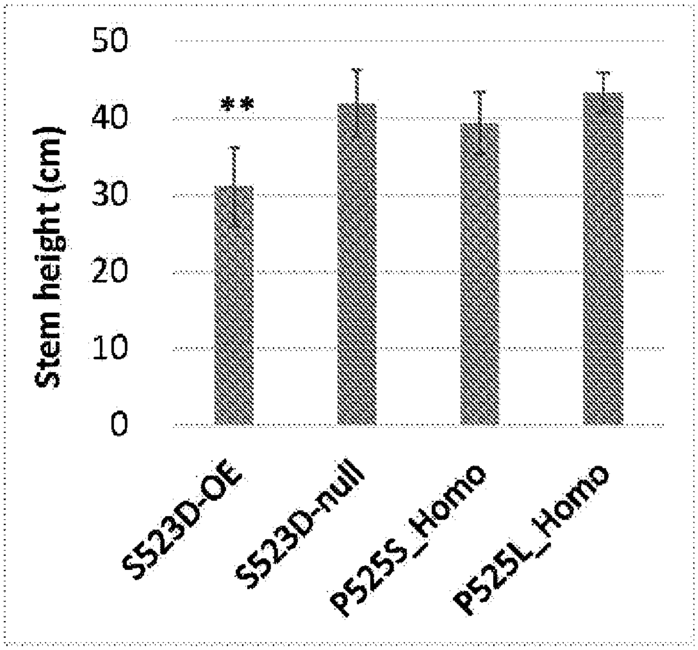
FIG. 19 is results of examining the stem heights of lines of T1 generation of S523D-OE, S523D-null, P525L-Homo, and P525S-Homo of Tsukuba1. The number of replications is 9 (S523D-OE and Null) or 6 (P525S and P525L), significant difference by the t-test: ** $P<0.01$, and error bars indicate standard deviations (SDs).

The number of leaves above the ground of the line highly expressing NIA2_S523D (S523D-OE) was less than that of the control (S523D-null) by one (FIG. 18). Meanwhile, the homozygotes having amino acid substitution mutations of P525L and P525S in NIA1 were equivalent to the control (S523D-null) therein. A difference in the stem height as well as the number of leaves above the ground was significantly seen only in the lines highly expressing NIA2_S523D (S523D-OE), and S523D-OE was lower than the control in the stem height as well as the number of leaves above the ground (FIG. 19).

Figure 20:
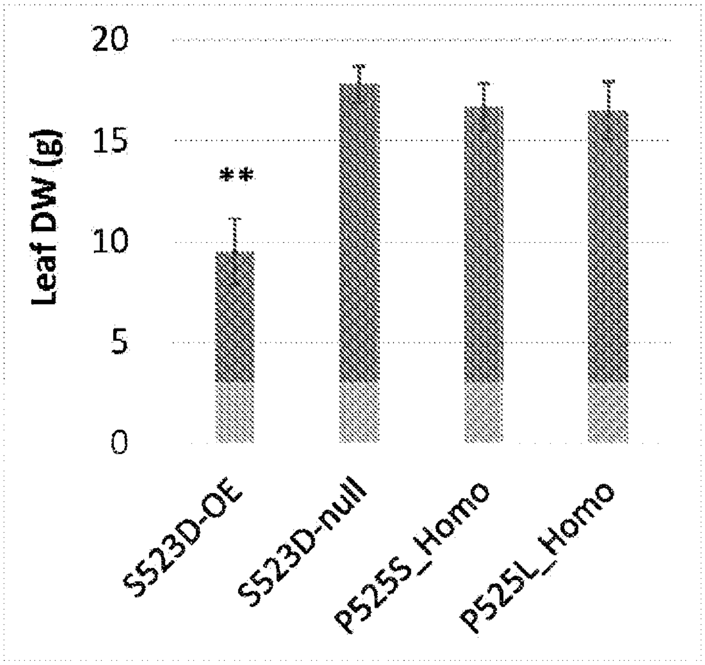
FIG. 20 is results of examining the dry matter weights of leaves above the ground (biomass) of lines of T1 generation of S523D-OE, S523D-null, P525L-Homo, and P525S-Homo of Tsukuba1. The number of replications is 9 (S523D-OE and Null) or 6 (P525S and P525L), significant difference by the t-test: ** $P<0.01$, and error bars indicate standard deviations (SDs).

The dry matter weight (biomass) of leaves above the ground of only the lines highly expressing NIA2_S523D (S523D-OE) was around a half of that of the control (S523D-null), and a significant difference therebetween was seen (FIG. 20).

From these results, markedly defective vegetation was also exhibited by highly expressing NIA2_S523D in the genetic background of Tsukuba1 (yellow species). Meanwhile, the abnormal vegetation was not seen in the homozygotes having the amino acid substitution mutations of P525L and P525S in NIA1 unlike the lines highly expressing NIA2_S523D (S523D-OE).

Figure 21:
FIG. 21 is a photograph showing anthesis 92 days after the sowing of lines of T1 generation of S523D-OE and S523D-null of Tsukuba1. Both were sown at the same time. The left is S523D-OE 13 days before anthesis, and the right is S523D-null 6 days after anthesis.

The cultivation was continued under the condition of constant 25° C. until the bloom, and the anthesis was also investigated. The bloom of the line highly expressing NIA2_S523D (S523D-OE) also tended to be later than that of the control (S523D-null) (FIG. 21).

Example 7 Components in Leaves of P525L and P525S Mutants Cultivated in Field (Nicotine and TSNAs)

A BC2F1 line obtained by further backcrossing the backcross line BC1F1, described in Example 5, with TN90 was isolated. BC2F3 generation obtained by self-pollination for two generation from this line was isolated and cultivated in a field. P525L_Homo and P525S_Homo are homozygotes having mutation of P525L or P525S in the NIA1 gene homozygously, respectively. P525L_WT and P525S_WT are lines isolated as individuals not having mutation in the NIA1 gene at BC2F2 generation respectively. The genotype of each separated line was determined by amplifying the NIA1_hingel region of the NIA1 gene by PCR and analyzing the nucleotide sequence thereof according to the method described in the selection of the EMS mutant in Example 1.

The cultivation was performed in the standard method for farming the Burley species (planting density: 2,380 plants/10 a, compound fertilizer Burley S625: 216 kg/10 a), and the compound fertilizer having 50% of the amount of the base fertilizer was added 8 days after the topping. Topping was carried out in the anthesis around 2 months after the transplantation, and lower leaves were then removed around three times. The two uppermost leaves were sampled 56 days after the topping and cured with a thermo-hygrostat (ESPEC CORP.) under the conditions described in Table 5.

TABLE 5

| | Yel-low-ing | Browning | | Stem drying | Condi-tion-ing |
|---|---|---|---|---|---|
| | | Program 1 | Program 2 | | |
| Temperature (° C.) | 38.0 | 32.0 | 32.0 | 50.0 | 22.0 |
| Relative humidity (%) | 85.0 | 93.0 | 89.0 | 40.0 | 60.0 |
| Curing period (hours) | 40.0 | 96.0 | 200.0 | 72.0 | 92.0 |

The cured leaves were ground, nicotine and tobacco-specific nitrosamines (TSNAs) were then analyzed using the dry powders as samples. To 0.25 g of a sample was added 4 ml of 2N sodium hydroxide, and the mixture was left to stand at room temperature for 30 minutes. Then, 40 ml of methanol was added for shaking extraction, and filtrate filtered through a 0.45 μm filter was measured for nicotine by gas chromatography-mass spectrometry (GC-MS) analysis.

To 0.5 g of a sample was added 20 ml of 0.1 M ammonium acetate for shaking extraction. The mixture was 10 times diluted with 0.1 M ammonium acetate, and four components (NNN, NAT, NAB, and NNK) of TSNA were then measured by liquid chromatography-mass spectrometry/mass spectrometry (LC-MS/MS) analysis.

Figure 22A:
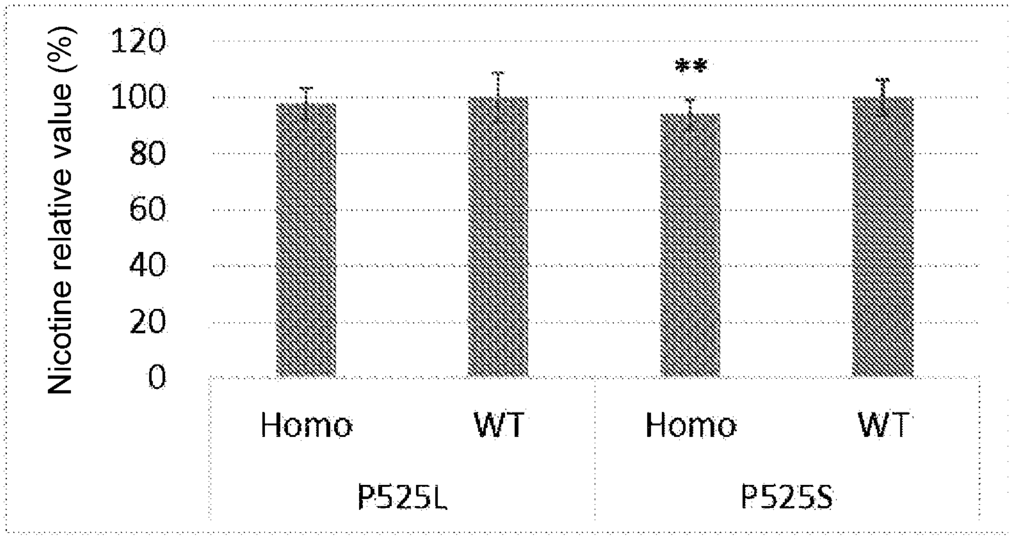
FIG. 22A shows the relative values (%) of the amounts of nicotine in cured leaves of a P525L mutant and a P525S mutant (BC2F3 generation) cultivated in a field. The relative values are relative values when the average values of the nicotine concentrations in cured leaves of WT are defined as 100 percent. The number of replications is 20 (only the number of replications of P525L Homo is 19), significant difference by the t-test: ** $P<0.01$, and error bars indicate standard deviations.
Figure 22B:
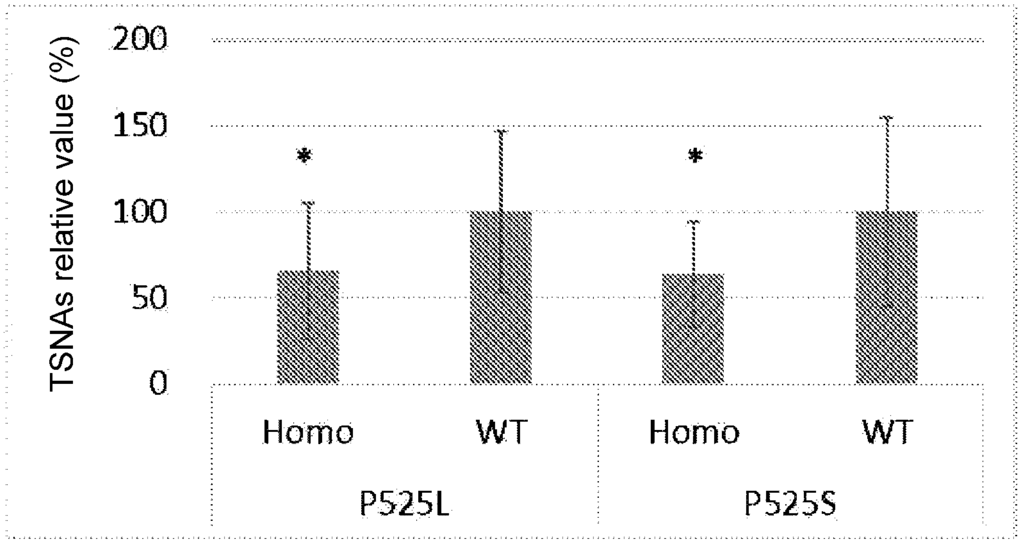
FIG. 22B shows the relative values (%) of the amounts of TSNAs in cured leaves of a P525L mutant and a P525S mutant (BC2F3 generation) cultivated in a field. The relative values are relative values when the average values of the TSNAs concentrations in cured leaves of WT is defined as 100 percent. The number of replications is 20 (only the number of replications of P525L Homo is 19), significant difference by the t-test: ** $P<0.01$, and error bars indicate standard deviations. The TSNAs is the total value of four TSNAs (NNN, NAT, NAB, and NNK).

Great difference in nicotine among P525L_Homo, P525S_Homo, and WT was not seen (FIG. 22A). The nicotine of the WTs of P525L and P525S were 6.3% and 5.8%, respectively. Meanwhile, a value obtained by totaling the analytical values of NNN, NAT, NAB, and NNK was defined as TSNAs for comparison. TSNAs in the homozygotes of both P525L and P525S decreased by 34 to 36% significantly as compared with the WTs (FIG. 22B). The TSNAs of the WTs of P525L and P525S were 3.8 ppm and 1.0 ppm, respectively. It was confirmed from these results that the TSNAs level in the cured leaves decreased due to a decrease in the nitric acid level in the mutants having mutations of P525L and P525S in the NIA1 gene.

INDUSTRIAL APPLICABILITY

The TSNA of tobacco raw materials and tobacco products can be reduced by utilizing a modified tobacco plant of the present invention in which the amount of nitrate accumulated decreases. The modified tobacco plant of the present invention not only has a decreased amount of nitric acid in leaves, but also preferably exhibits good plant growth. This can be utilized as a material of leaf tobacco for producing tobacco products.

The invention claimed is:

1. A tobacco plant comprising a nitrate reductase in which the amino acid residue corresponding to position 525 in an amino acid sequence having 90% or more sequence identity with—the amino acid sequence of SEQ ID NO: 2 or 4 is mutated from proline to leucine or serine, wherein the tobacco plant has the properties (a) to (c):

(a) activity of the nitrate reductase under a dark condition is 80% or more of activity of the nitrate reductase under a light condition;

(b) growth characteristics of an individual plant for height of the plant, number of leaves on the plant, the size of leaves on the plant and the dry matter weight of leaves above the ground are the same as or the difference is 20% or less different from a control; and (c) nitric acid decreases as compared with the control, and wherein the control is a tobacco plant comprising a nitrate reductase consisting of the amino acid sequence of SEQ ID NO: 2 or 4.

2. The tobacco plant according to claim 1, wherein the amino acid residue corresponding to position 525 in an amino acid sequence having 90% or more sequence identity with the amino acid sequence of SEQ ID NO: 2 or 4 is mutated from proline to—serine.

3. The tobacco plant according to claim 1, wherein the mutated nitrate reductase has an amino acid sequence that is has 95% or more sequence identity with the amino acid sequence of SEQ ID NO: 2 or 4.

4. The tobacco plant according to claim 1, wherein the mutated nitrate reductase has the amino acid sequence of any one of SEQ ID NOs: 5 to 8.

5. The tobacco plant according to claim 1, wherein nitric acid decreases in leaf tissue by at least 10% as compared with the control, as determined by a quantification method that measures nitric acid levels in plant tissue.

6. The tobacco plant according to claim 1, wherein the tobacco plant is *Nicotiana tabacum.*

7. A method for producing the tobacco plant according to claim 1, comprising:

(i) modifying the amino acid residue corresponding to position 525 in an amino acid sequence having 90% or more sequence identity with the amino acid sequence of SEQ ID NO: 2 or 4 of a nitrate reductase of a tobacco plant from proline to leucine or serine, or selecting a tobacco plant in which the amino acid residue corresponding to position 525 in the amino acid sequence having 90% or more sequence identity with the amino acid sequence of SEQ ID NO: 2 or 4 of the nitrate reductase is mutated from proline to leucine or serine by mutation, wherein the tobacco plant has the properties (a) to (c):

(a) activity of the nitrate reductase under a dark condition is 80% or more of activity of the nitrate reductase under a light condition;

(b) growth characteristics of an individual plant for height of the plant, number of leaves on the plant, the size of leaves on the plant and the dry matter weight of leaves above the ground are the same as or the difference is 20% or less different from a control; and (c) nitric acid decreases as compared with the control, and wherein the control is a tobacco plant comprising a nitrate reductase consisting of the amino acid sequence of SEQ ID NO: 2 or 4.

8. Leaf tobacco harvested from the tobacco plant according to claim 1.

9. A cured leaf generated from the leaf tobacco according to claim 8.

10. A cut filler, powder, a sheet, a stem, granules, or an extract produced from the cured leaf according to claim 9, wherein the cut filler, powder, sheet, stem, granules, or extract comprises a nitrate reductase in which the amino acid residue corresponding to position 525 in an amino acid sequence having 90% or more sequence identity to SEQ ID NO: 2 or 4 is mutated from proline to leucine or serine.

11. A tobacco product comprising the cured leaf according to claim 9.

12. A tobacco product comprising the cut filler, the powder, the sheet, the stem, the granules, or the extract according to claim 10.

* * * * *

SEQUENCE LISTING

```
Sequence total quantity: 25
SEQ ID NO: 1            moltype = DNA  length = 2715
FEATURE                 Location/Qualifiers
source                  1..2715
                        mol_type = other DNA
                        organism = Nicotiana tabacum
CDS                     1..2715
SEQUENCE: 1
atggcggcat ctgtcgaaaa caggcagttc agtcacatag aagccggttt atcccggtct  60
ttcaagcctc ggtctgattc cccggttcgt ggctgcaact tccctccgcc caacagtact  120
aatttccaaa agaaaccaaa ttccaccatt ttccttgatt actcgtcgag tgaagacgac  180
gatgatgatg acgaaaaaaa tgagtacctt caaatgatca aaaaagggaa ttcagaatta  240
gagccatctg ttcatgacag cagggacgaa ggtaccgctg ataactggat tgaacgcaac  300
ttttccttga ttcgtctcac cggaaagcat ccatttaact ccgaaccgcc gttgaaccgt  360
ctcatgcacc acggttttat cacaccggtc ccacttcatt acgttcgtaa ccatggaccg  420
gttcccaagg gcacatggga tgactggacc gtggaagtca cgggactagt gaaacgtcct  480
atgaaattca caatggacca gttggttaac gaattccctt ccagagaatt gcccgttacg  540
cttgtgtgtg ctggcaaccg aaggaaagaa cagaacatgg ttaaacaaac cattggtttc  600
aactggggtg ccgctgccgt ttcaacaact gtatggcgcg gggtacccct acgcgctttg  660
ttaaaacggt gcggtgtttt tagcaagaat aaaggggcgc ttaatgtttg cttcgaagga  720
gctgatgtct tgcccggagg cggtggttca aagtatggaa ccagcattaa gaaggaattt  780
gcaatggatc cagcacgaga tatcataata gcttacatgc agaacggaga aaaattggca  840
cccgaccacg ggtttccagt acgaatgata attccaggat tcattggagg aagaatggtg  900
aaatggataa agaggattat agtcaccacc caagaatcag acagctatta tcatttcaag  960
gacaatagag ttcttcctcc ccatgttgat gctgaacttg caaatactga agcatggtgg  1020
tacaagccag agtacatcat caatgagctc aatattaact ctgtcattac gacgccgtgt  1080
catgaagaaa ttttgcctat taacgcctgg acgactcagc gaccttacac gttgaggggc  1140
tattcttatt ctggcggagg gaaaaaagta acgcgagtag aagtgacctt ggatggagga  1200
gaaacatggc aagtttgcac actagatcac ccagagaagc ccaccaaata tggcaagtac  1260
tggtgttggt gcttttggtc actcgaggtt gaggtgttag acttgctcag tgccaaagaa  1320
attgctgttc gagcttggga tgagaccctc aatactcaac ctgagaagct tatttggaat  1380
gtcatgggaa tgatgaacaa ttgctggttc cgagtaaaga tgaatgtgtg caagcctcac  1440
aagggagaga ttggaatagt gtttgaacac ccgactcaac ctggaaacca atcaggtgga  1500
tggatggcaa aggagaggca tttggagata tcagcagagg cacctccaac actaaagaag  1560
agtatctcaa ctccattcat gaacacagct tccaagatgt actccatgtc ggaggtgagg  1620
aaacacagct ctgctgactc tgcttggatc atagtccatg gtcatatcta tgacgccacg  1680
cgtttcttga aagatcaccc cggtggttct gacagcattc tcatcaatgc tggcactgat  1740
tgcactgagg aatttgatgc aattcattct gataaggcta agaagctatt ggaggaattc  1800
aggattggtg aactcataac tactggttac acctctgact ctcctggcaa ctccgtccat  1860
ggatcttctt ccttcagcag ctttctagca cctattaagg aacttgttcc agcgcagagg  1920
agtgtggccc tcattccaag agagaaaatc ccatgcaaac tcatcgacaa acaatccatc  1980
tcccctgatg ttaggaaatt tcgatttgca ttgccctctg aggatcaagt cttgggcttg  2040
cctgttggta aacacatctt cctctgtgcc gttattgacg ataagctctg catgcgcgcc  2100
tacacgccta ctagcacgat cgatgaggtg gggtacttcg agttggttgt caagatatac  2160
ttcaaaggaa ttcaccctaa attccccaat gggggcaaa tgtcacaata ccttgattct  2220
ctccaattag ggtcatttct cgacgtgaaa ggtccattag gtcacattga ataccaagga  2280
```

```
aagggcaatt tcttagttca tggcaaacaa aagtttgcca agaagttggc catgatagca  2340
ggtggaacag ggataactcc agtttatcaa gtcatgcagg caattctgaa agatccagaa  2400
gatgacacag aaatgtatgt ggtctatgct aatagaacag aggatgatat tttacttaag  2460
gaagagcttg attcatgggc tgagaaaatt ccagaaaggg ttaaagtttg gtatgtggtt  2520
caagattcta ttaaagaagg atggaagtac agccttggtt ttatttcaga agccattttg  2580
agagaacata tccctgagcc atctcacaca acactggctt tggcttgtgg accacctcct  2640
atgattcaat ttgctgttaa tccaaacttg gagaagatgg gctatgacat taaggattcc  2700
ttattggtgt tctaa                                                   2715

SEQ ID NO: 2           moltype = AA  length = 904
FEATURE                Location/Qualifiers
source                 1..904
                       mol_type = protein
                       organism = Nicotiana tabacum
SEQUENCE: 2
MAASVENRQF SHIEAGLSRS FKPRSDSPVR GCNFPPPNST NFQKKPNSTI FLDYSSSEDD  60
DDDDEKNEYL QMIKKGNSEL EPSVHDSRDE GTADNWIERN FSLIRLTGKH PFNSEPPLNR  120
LMHHGFITPV PLHYVRNHGP VPKGTWDDWT VEVTGLVKRP MKFTMDQLVN EFPSRELPVT  180
LVCAGNRRKE QNMVKQTIGF NWGAAAVSTT VWRGVPLRAL LKRCGVFSKN KGALNVCFEG  240
ADVLPGGGGS KYGTSIKKEF AMDPARDIII AYMQNGEKLA PDHGFPVRMI IPGFIGGRMV  300
KWIKRIIVTT QESDSYYHFK DNRVLPPHVD AELANTEAWW YKPEYIINEL NINSVITTPC  360
HEEILPINAW TTQRPYTLRG YSYSGGGKKV TRVEVTLDGG ETWQVCTLDH PEKPTKYGKY  420
WCWCFWSLEV EVLDLLSAKE IAVRAWDETL NTQPEKLIWN VMGMMNNCWF RVKMNVCKPH  480
KGEIGIVFEH PTQPGNQSGG WMAKERHLEI SAEAPPTLKK SISTPFMNTA SKMYSMSEVR  540
KHSSADSAWI IVHGHIYDAT RFLKDHPGGS DSILINAGTD CTEEFDAIHS DKAKKLLEEF  600
RIGELITTGY TSDSPGNSVH GSSSFSSFLA PIKELVPAQR SVALIPREKI PCKLIDKQSI  660
SPDVRKFRFA LPSEDQVLGL PVGKHIFLCA VIDDKLCMRA YTPTSTIDEV GYFELVVKIY  720
FKGIHPKFPN GGQMSQYLDS LQLGSFLDVK GPLGHIEYQG KGNFLVHGKQ KFAKKLAMIA  780
GGTGITPVYQ VMQAILKDPE DDTEMYVVYA NRTEDDILLK EELDSWAEKI PERVKVWYVV  840
QDSIKEGWKY SLGFISEAIL REHIPEPSHT TLALACGPPP MIQFAVNPNL EKMGYDIKDS  900
LLVF                                                               904

SEQ ID NO: 3           moltype = DNA  length = 2715
FEATURE                Location/Qualifiers
source                 1..2715
                       mol_type = other DNA
                       organism = Nicotiana tabacum
CDS                    1..2715
SEQUENCE: 3
atggcggcat ctgtcgaaaa caggcagttc agtcacctag aagccggttt atcccggtct  60
ttcaagcccc ggtctgattc cccggttcgt ggctgcaact tcccttcgcc caacagtact  120
aatttccaaa agaaaccaaa ttccaccatt taccttgatt actcgtcgag tgaagacgac  180
gatgatgatg acgaaaaaaa tgagtacctt caaatgatta aaaaagggaa ttcagagtta  240
gagccatctg ttcatgacac tagggacgaa ggtaccgctg ataattggat tgaacgcaac  300
ttttccatga ttcgtctcac cggaaagcat ccatttaact ccgaaccacc gttgaaccgg  360
ctcatgcacc acggctttat cacaccggtc ccacttcatt acgttcgtaa ccatggaccg  420
gttcccaagg gcacgtggga tgactggacc gtggaagtca cgggactagt gaagcgtcct  480
atgaaattca caatggacca gttggttaac gaattccctt gtagagaatt gcccgttacg  540
cttgtttgtg ctggcaatcg aaggaaagaa cagaacatgg ttaaacaaac cattggtttc  600
aactggggcg ccgctgccgt ttcaacaacg atatggcgcg gggtacccct ccgcgctttg  660
ctaaaacggt gcggtgtttt tagcaagaat aaaggggcgc ttaatgtttg cttcgaagga  720
gctgatgtgt tgcccggagg tggtggttca aagtatggaa ccagcattaa gaaggaattt  780
gcaatggatc cagcacgaga tatcatcgta gcctacatgc agaacggaga aaaattggca  840
cccgaccacg ggtttccagt acgaatgata attccaggat tcattggagg aagaatggtg  900
aaatggataa agaggattat agtcaccacc caagaatcag acagctatta tcatttcaag  960
gacaatagag ttcttcctcc ccatgttgat gctgaacttg caaataccga agcatggtgg  1020
tacaagccag agtatatcat caatgagctt aatattaact ctgtcattac gacgccgtgt  1080
catgaagaaa ttttgccaat taacgcctgg acgactcagc gaccttacac gttgaggggc  1140
tattcttatt ctggcggagg gaaaaaagta acgcgagtag aagtgacgtt ggatggagga  1200
gaaacatggc aagttagcac actagatcac ccagagaagc ccaccaaata tggcaagtac  1260
tggtgttggt gcttttggtc actcgaggtt gaggtgttag acttgctcag tgctaaagaa  1320
attgctgttc gagcttggga tgagaccctc aatactcaac ccgagaagct tatttggaac  1380
gtcatgggaa tgatgaataa ttgctggttc cgagtaaaga tgaatgtgtg caagcctcac  1440
aagggagaga ttggaatagt gtttgagcat ccgactcaac ctggaaacca atcaggtgga  1500
tggatggcga aggagagaca tttggagata tcagcagagg cacctcaaac actaaagaag  1560
agtatctcaa ctccattcat gaacacagct tccaagatgt actccatgtc cgaggtcagg  1620
aaacacagct ctgctgactc tgcttggatc atagtccatg gtcatatcta tgacgccacg  1680
cgtttcttga aagatcaccc tggtgggact gacagcattc tcatcaatgc tggcactgat  1740
tgcactgagg aatttgatgc aattcattct gataaggcta agaagctctt ggaggatttc  1800
aggattggtg aactcataac tactggttac acctctgact ctcctggcaa ctccgtgcac  1860
ggatcttctt ccttcagcag ctttctagca cctattaagg aacttgttcc agcgcagagg  1920
agtgtggccc taattccaag agagaaaatc ccatgcaaac tcatcgacaa gcaatccatc  1980
tcccatgatg ttaggaaatt tcgatttgca ttgccctctg aggatcaagt cttgggcttg  2040
cctgttggaa aacatatctt cctctgtgcc gttattgacg ataagctctg catgcgcgct  2100
tacacgccta ctagcacgat cgatgaggtg gggtacttcg agttggttgt caagatatac  2160
ttcaaaggaa ttcaccctaa attccccaat ggagggcaaa tgtcacagta tcttgattct  2220
atgccgttag ggtcatttct cgacgtgaaa ggtccattag gtcacattga ataccaagga  2280
aagggaaatt tcttagttca tggcaaacag aagtttgcca agaagttggc catgatagca  2340
ggtggaacag gaataactcc agtgtatcaa gtcatgcagg caattctgaa agatccagaa  2400
```

-continued

```
gatgacacag aaatgtatgt ggtgtatgct aacagaacag aggatgatat tttacttaag  2460
gaagagcttg attcatgggc tgagaaaatt ccagagaggg ttaaagtttg gtatgtggtt  2520
caggattcta ttaaagaagg atggaagtac agcattggtt ttattacaga agccattttg  2580
agagaacata tccctgagcc atctcacaca acactggctt tggcttgtgg accacctcct  2640
atgattcaat ttgctgttaa tccaaacttg gagaagatgg gctatgacat taaggattcc  2700
ttattggtgt tctaa                                                   2715

SEQ ID NO: 4           moltype = AA  length = 904
FEATURE                Location/Qualifiers
source                 1..904
                       mol_type = protein
                       organism = Nicotiana tabacum
SEQUENCE: 4
MAASVENRQF SHLEAGLSRS FKPRSDSPVR GCNFPSPNST NFQKKPNSTI YLDYSSSEDD  60
DDDDEKNEYL QMIKKGNSEL EPSVHDTRDE GTADNWIERN FSMIRLTGKH PFNSEPPLNR  120
LMHHGFITPV PLHYVRNHGP VPKGTWDDWT VEVTGLVKRP MKFTMDQLVN EFPCRELPVT  180
LVCAGNRRKE QNMVKQTIGF NWGAAAVSTT IWRGVPLRAL LKRCGVFSKN KGALNVCFEG  240
ADVLPGGGGS KYGTSIKKEF AMDPARDIIV AYMQNGEKLA PDHGFPVRMI IPGFIGGRMV  300
KWIKRIIVTT QESDSYYHFK DNRVLPPHVD AELANTEAWW YKPEYIINEL NINSVITTPC  360
HEEILPINAW TTQRPYTLRG YSYSGGGKKV TRVEVTLDGG ETWQVSTLDH PEKPTKYGKY  420
WCWCFWSLEV EVLDLLSAKE IAVRAWDETL NTQPEKLIWN VMGMMNNCWF RVKMNVCKPH  480
KGEIGIVFEH PTQPGNQSGG WMAKERHLEI SAEAPQTLKK SISTPFMNTA SKMYSMSEVR  540
KHSSADSAWI IVHGHIYDAT RFLKDHPGGT DSILINAGTD CTEEFDAIHS DKAKKLLEDF  600
RIGELITTGY TSDSPGNSVH GSSSFSSFLA PIKELVPAQR SVALIPREKI PCKLIDKQSI  660
SHDVRKFRFA LPSEDQVLGL PVGKHIFLCA VIDDKLCMRA YTPTSTIDEV GYFELVVKIY  720
FKGIHPKFPN GGQMSQYLDS MPLGSFLDVK GPLGHIEYQG KGNFLVHGKQ KFAKKLAMIA  780
GGTGITPVYQ VMQAILKDPE DDTEMYVVYA NRTEDDILLK EELDSWAEKI PERVKVWYVV  840
QDSIKEGWKY SIGFITEAIL REHIPEPSHT TLALACGPPP MIQFAVNPNL EKMGYDIKDS  900
LLVF                                                               904

SEQ ID NO: 5           moltype = AA  length = 904
FEATURE                Location/Qualifiers
source                 1..904
                       mol_type = protein
                       organism = Nicotiana tabacum
SEQUENCE: 5
MAASVENRQF SHIEAGLSRS FKPRSDSPVR GCNFPPPNST NFQKKPNSTI FLDYSSSEDD  60
DDDDEKNEYL QMIKKGNSEL EPSVHDSRDE GTADNWIERN FSLIRLTGKH PFNSEPPLNR  120
LMHHGFITPV PLHYVRNHGP VPKGTWDDWT VEVTGLVKRP MKFTMDQLVN EFPSRELPVT  180
LVCAGNRRKE QNMVKQTIGF NWGAAAVSTT VWRGVPLRAL LKRCGVFSKN KGALNVCFEG  240
ADVLPGGGGS KYGTSIKKEF AMDPARDIII AYMQNGEKLA PDHGFPVRMI IPGFIGGRMV  300
KWIKRIIVTT QESDSYYHFK DNRVLPPHVD AELANTEAWW YKPEYIINEL NINSVITTPC  360
HEEILPINAW TTQRPYTLRG YSYSGGGKKV TRVEVTLDGG ETWQVCTLDH PEKPTKYGKY  420
WCWCFWSLEV EVLDLLSAKE IAVRAWDETL NTQPEKLIWN VMGMMNNCWF RVKMNVCKPH  480
KGEIGIVFEH PTQPGNQSGG WMAKERHLEI SAEAPPTLKK SISTLFMNTA SKMYSMSEVR  540
KHSSADSAWI IVHGHIYDAT RFLKDHPGGS DSILINAGTD CTEEFDAIHS DKAKKLLEEF  600
RIGELITTGY TSDSPGNSVH GSSSFSSFLA PIKELVPAQR SVALIPREKI PCKLIDKQSI  660
SPDVRKFRFA LPSEDQVLGL PVGKHIFLCA VIDDKLCMRA YTPTSTIDEV GYFELVVKIY  720
FKGIHPKFPN GGQMSQYLDS LQLGSFLDVK GPLGHIEYQG KGNFLVHGKQ KFAKKLAMIA  780
GGTGITPVYQ VMQAILKDPE DDTEMYVVYA NRTEDDILLK EELDSWAEKI PERVKVWYVV  840
QDSIKEGWKY SLGFISEAIL REHIPEPSHT TLALACGPPP MIQFAVNPNL EKMGYDIKDS  900
LLVF                                                               904

SEQ ID NO: 6           moltype = AA  length = 904
FEATURE                Location/Qualifiers
source                 1..904
                       mol_type = protein
                       organism = Nicotiana tabacum
SEQUENCE: 6
MAASVENRQF SHLEAGLSRS FKPRSDSPVR GCNFPSPNST NFQKKPNSTI YLDYSSSEDD  60
DDDDEKNEYL QMIKKGNSEL EPSVHDTRDE GTADNWIERN FSMIRLTGKH PFNSEPPLNR  120
LMHHGFITPV PLHYVRNHGP VPKGTWDDWT VEVTGLVKRP MKFTMDQLVN EFPCRELPVT  180
LVCAGNRRKE QNMVKQTIGF NWGAAAVSTT IWRGVPLRAL LKRCGVFSKN KGALNVCFEG  240
ADVLPGGGGS KYGTSIKKEF AMDPARDIIV AYMQNGEKLA PDHGFPVRMI IPGFIGGRMV  300
KWIKRIIVTT QESDSYYHFK DNRVLPPHVD AELANTEAWW YKPEYIINEL NINSVITTPC  360
HEEILPINAW TTQRPYTLRG YSYSGGGKKV TRVEVTLDGG ETWQVSTLDH PEKPTKYGKY  420
WCWCFWSLEV EVLDLLSAKE IAVRAWDETL NTQPEKLIWN VMGMMNNCWF RVKMNVCKPH  480
KGEIGIVFEH PTQPGNQSGG WMAKERHLEI SAEAPQTLKK SISTLFMNTA SKMYSMSEVR  540
KHSSADSAWI IVHGHIYDAT RFLKDHPGGT DSILINAGTD CTEEFDAIHS DKAKKLLEDF  600
RIGELITTGY TSDSPGNSVH GSSSFSSFLA PIKELVPAQR SVALIPREKI PCKLIDKQSI  660
SHDVRKFRFA LPSEDQVLGL PVGKHIFLCA VIDDKLCMRA YTPTSTIDEV GYFELVVKIY  720
FKGIHPKFPN GGQMSQYLDS MPLGSFLDVK GPLGHIEYQG KGNFLVHGKQ KFAKKLAMIA  780
GGTGITPVYQ VMQAILKDPE DDTEMYVVYA NRTEDDILLK EELDSWAEKI PERVKVWYVV  840
QDSIKEGWKY SIGFITEAIL REHIPEPSHT TLALACGPPP MIQFAVNPNL EKMGYDIKDS  900
LLVF                                                               904

SEQ ID NO: 7           moltype = AA  length = 904
FEATURE                Location/Qualifiers
source                 1..904
```

```
                       mol_type = protein
                       organism = Nicotiana tabacum
SEQUENCE: 7
MAASVENRQF SHIEAGLSRS FKPRSDSPVR GCNFPPPNST NFQKKPNSTI FLDYSSSEDD  60
DDDDEKNEYL QMIKKGNSEL EPSVHDSRDE GTADNWIERN FSLIRLTGKH PFNSEPPLNR  120
LMHHGFITPV PLHYVRNHGP VPKGTWDDWT VEVTGLVKRP MKFTMDQLVN EFPSRELPVT  180
LVCAGNRRKE QNMVKQTIGF NWGAAAVSTT VWRGVPLRAL LKRCGVFSKN KGALNVCFEG  240
ADVLPGGGGS KYGTSIKKEF AMDPARDIII AYMQNGEKLA PDHGFPVRMI IPGFIGGRMV  300
KWIKRIIVTT QESDSYYHFK DNRVLPPHVD AELANTEAWW YKPEYIINEL NINSVITTPC  360
HEEILPINAW TTQRPYTLRG YSYSGGGKKV TRVEVTLDGG ETWQVCTLDH PEKPTKYGKY  420
WCWCFWSLEV EVLDLLSAKE IAVRAWDETL NTQPEKLIWN VMGMMNNCWF RVKMNVCKPH  480
KGEIGIVFEH PTQPGNQSGG WMAKERHLEI SAEAPPTLKK SISTSFMNTA SKMYSMSEVR  540
KHSSADSAWI IVHGHIYDAT RFLKDHPGGS DSILINAGTD CTEEFDAIHS DKAKKLLEEF  600
RIGELITTGY TSDSPGNSVH GSSSFSSFLA PIKELVPAQR SVALIPREKI PCKLIDKQSI  660
SPDVRKFRFA LPSEDQVLGL PVGKHIFLCA VIDDKLCMRA YTPTSTIDEV GYFELVVKIY  720
FKGIHPKFPN GGQMSQYLDS LQLGSFLDVK GPLGHIEYQG KGNFLVHGKQ KFAKKLAMIA  780
GGTGITPVYQ VMQAILKDPE DDTEMYVVYA NRTEDDILLK EELDSWAEKI PERVKVWYVV  840
QDSIKEGWKY SLGFISEAIL REHIPEPSHT TLALACGPPP MIQFAVNPNL EKMGYDIKDS  900
LLVF                                                              904

SEQ ID NO: 8           moltype = AA  length = 904
FEATURE                Location/Qualifiers
source                 1..904
                       mol_type = protein
                       organism = Nicotiana tabacum
SEQUENCE: 8
MAASVENRQF SHLEAGLSRS FKPRSDSPVR GCNFPSPNST NFQKKPNSTI YLDYSSSEDD  60
DDDDEKNEYL QMIKKGNSEL EPSVHDTRDE GTADNWIERN FSMIRLTGKH PFNSEPPLNR  120
LMHHGFITPV PLHYVRNHGP VPKGTWDDWT VEVTGLVKRP MKFTMDQLVN EFPCRELPVT  180
LVCAGNRRKE QNMVKQTIGF NWGAAAVSTT IWRGVPLRAL LKRCGVFSKN KGALNVCFEG  240
ADVLPGGGGS KYGTSIKKEF AMDPARDIIV AYMQNGEKLA PDHGFPVRMI IPGFIGGRMV  300
KWIKRIIVTT QESDSYYHFK DNRVLPPHVD AELANTEAWW YKPEYIINEL NINSVITTPC  360
HEEILPINAW TTQRPYTLRG YSYSGGGKKV TRVEVTLDGG ETWQVSTLDH PEKPTKYGKY  420
WCWCFWSLEV EVLDLLSAKE IAVRAWDETL NTQPEKLIWN VMGMMNNCWF RVKMNVCKPH  480
KGEIGIVFEH PTQPGNQSGG WMAKERHLEI SAEAPQTLKK SISTSFMNTA SKMYSMSEVR  540
KHSSADSAWI IVHGHIYDAT RFLKDHPGGT DSILINAGTD CTEEFDAIHS DKAKKLLEDF  600
RIGELITTGY TSDSPGNSVH GSSSFSSFLA PIKELVPAQR SVALIPREKI PCKLIDKQSI  660
SHDVRKFRFA LPSEDQVLGL PVGKHIFLCA VIDDKLCMRA YTPTSTIDEV GYFELVVKIY  720
FKGIHPKFPN GGQMSQYLDS MPLGSFLDVK GPLGHIEYQG KGNFLVHGKQ KFAKKLAMIA  780
GGTGITPVYQ VMQAILKDPE DDTEMYVVYA NRTEDDILLK EELDSWAEKI PERVKVWYVV  840
QDSIKEGWKY SIGFITEAIL REHIPEPSHT TLALACGPPP MIQFAVNPNL EKMGYDIKDS  900
LLVF                                                              904

SEQ ID NO: 9           moltype = DNA  length = 20
FEATURE                Location/Qualifiers
misc_feature           1..20
                       note = primer for sequencing Nia2_ex1_2F
source                 1..20
                       mol_type = other DNA
                       organism = synthetic construct
SEQUENCE: 9
accgaagcat ggtggtacaa                                             20

SEQ ID NO: 10          moltype = DNA  length = 22
FEATURE                Location/Qualifiers
misc_feature           1..22
                       note = primer for sequencing Nia2_ex2_3F
source                 1..22
                       mol_type = other DNA
                       organism = synthetic construct
SEQUENCE: 10
ggctattctt attctggcgg ag                                          22

SEQ ID NO: 11          moltype = DNA  length = 20
FEATURE                Location/Qualifiers
misc_feature           1..20
                       note = primer for sequencing Nia2_ex3_4R
source                 1..20
                       mol_type = other DNA
                       organism = synthetic construct
SEQUENCE: 11
catcattccc atgacgttcc                                             20

SEQ ID NO: 12          moltype = DNA  length = 21
FEATURE                Location/Qualifiers
misc_feature           1..21
                       note = primer for sequencing Nia2_ex4_HindIII_R
source                 1..21
                       mol_type = other DNA
```

```
                        organism = synthetic construct
SEQUENCE: 12
gctgctgaag cttgaagatc c                                                21

SEQ ID NO: 13           moltype = DNA  length = 24
FEATURE                 Location/Qualifiers
misc_feature            1..24
                        note = primer NRs_TMF
source                  1..24
                        mol_type = other DNA
                        organism = synthetic construct
SEQUENCE: 13
caggattggt gaactcataa ctac                                             24

SEQ ID NO: 14           moltype = DNA  length = 18
FEATURE                 Location/Qualifiers
misc_feature            1..18
                        note = primer NRs_TMR
source                  1..18
                        mol_type = other DNA
                        organism = synthetic construct
SEQUENCE: 14
ctctgcgctg gaacaagt                                                    18

SEQ ID NO: 15           moltype = DNA  length = 20
FEATURE                 Location/Qualifiers
misc_feature            1..20
                        note = probe NRs_wt_WGB
source                  1..20
                        mol_type = other DNA
                        organism = synthetic construct
SEQUENCE: 15
gatcttcttc cttcagcagc                                                  20

SEQ ID NO: 16           moltype = DNA  length = 20
FEATURE                 Location/Qualifiers
misc_feature            1..20
                        note = probe NRs_tg_MGB
source                  1..20
                        mol_type = other DNA
                        organism = synthetic construct
SEQUENCE: 16
ggatcttcaa gcttcagcag                                                  20

SEQ ID NO: 17           moltype = DNA  length = 20
FEATURE                 Location/Qualifiers
misc_feature            1..20
                        note = primer elfa_v2_TMF
source                  1..20
                        mol_type = other DNA
                        organism = synthetic construct
SEQUENCE: 17
ctaagggtgc tgccagcttt                                                  20

SEQ ID NO: 18           moltype = DNA  length = 22
FEATURE                 Location/Qualifiers
misc_feature            1..22
                        note = primer elfa_v2_TMR
source                  1..22
                        mol_type = other DNA
                        organism = synthetic construct
SEQUENCE: 18
gtcaagcact ggagcatatc ca                                               22

SEQ ID NO: 19           moltype = DNA  length = 26
FEATURE                 Location/Qualifiers
misc_feature            1..26
                        note = probe elfa_v2_TMP
source                  1..26
                        mol_type = other DNA
                        organism = synthetic construct
SEQUENCE: 19
atcatgaacc atccaggaca gattgg                                           26

SEQ ID NO: 20           moltype = DNA  length = 24
FEATURE                 Location/Qualifiers
misc_feature            1..24
                        note = primer NIA1_hinge1_F2
source                  1..24
```

```
                         mol_type = other DNA
                         organism = synthetic construct
SEQUENCE: 20
ttaggtgaaa taacgctctt acac                                            24

SEQ ID NO: 21            moltype = DNA  length = 24
FEATURE                  Location/Qualifiers
misc_feature             1..24
                         note = primer NIA1_hinge1_R2
source                   1..24
                         mol_type = other DNA
                         organism = synthetic construct
SEQUENCE: 21
cctaattgga gagaatcaag gtat                                            24

SEQ ID NO: 22            moltype = DNA  length = 24
FEATURE                  Location/Qualifiers
misc_feature             1..24
                         note = primer NIA2_hinge1_F2
source                   1..24
                         mol_type = other DNA
                         organism = synthetic construct
SEQUENCE: 22
attgtgctat gttgcaatgt tcag                                            24

SEQ ID NO: 23            moltype = DNA  length = 19
FEATURE                  Location/Qualifiers
misc_feature             1..19
                         note = primer NIA2_hinge1_R1
source                   1..19
                         mol_type = other DNA
                         organism = synthetic construct
SEQUENCE: 23
ggaagaagat ccgtgcacg                                                  19

SEQ ID NO: 24            moltype = DNA  length = 2724
FEATURE                  Location/Qualifiers
source                   1..2724
                         mol_type = other DNA
                         organism = Nicotiana tabacum
CDS                      4..2718
SEQUENCE: 24
catatggcgg catctgtcga aaacaggcag ttcagtcacc tagaagccgg tttatcccgg  60
tctttcaagc cccggtctga ttccccggtt cgtggctgca acttcccttc gcccaacagt  120
actaatttcc aaaagaaacc aaattccacc atttaccttg attactcgtc gagtgaagac  180
gacgatgatg atgacgaaaa aaatgagtac cttcaaatga ttaaaaaagg gaattcagag  240
ttagagccat ctgttcatga cactagggac gaaggtaccg ctgataattg gattgaacgc  300
aacttttcca tgattcgtct caccggaaag catccattta actccgaacc accgttgaac  360
cggctcatgc accacggctt tatcacaccg gtcccacttc attacgttcg taaccatgga  420
ccggttccca agggcacgtg ggatgactgg accgtggaag tcacgggact agtgaagcgt  480
cctatgaaat tcacaatgga ccagttggtt aacgaattcc cttgtagaga attgcccgtt  540
acgcttgttt gtgctggcaa tcgaaggaaa gaacagaaca tggttaaaca aaccattggt  600
ttcaactggg gcgccgctgc cgtttcaaca acgatatggc gcggggtacc cctccgcgct  660
ttgctaaaac ggtgcggtgt ttttagcaag aataaagggg cgcttaatgt ttgcttcgaa  720
ggagctgatg tgttgcccgg aggtggtggt tcaaagtatg gaaccagcat taagaaggaa  780
tttgcaatgg atccagcacg agatatcatc gtagcctaca tgcagaacgg agaaaaattg  840
gcacccgacc acgggtttcc agtacgaatg ataattccag gattcattgg aggaagaatg  900
gtgaaatgga taaagaggat tatagtcacc acccaagaat cagacagcta ttatcatttc  960
aaggacaata gagttcttcc tccccatgtt gatgctgaac ttgcaaatac cgaagcatgg  1020
tggtacaagc cagagtatat catcaatgag cttaatatta actctgtcat tacgacgccg  1080
tgtcatgaag aaattttgcc aattaacgcc tggacgactc agcgacctta cacgttgagg  1140
ggctattctt attctggcgg agggaaaaaa gtaacgcgag tagaagtgac gttggatgga  1200
ggagaaacat ggcaagttag cacactagat cacccagaga agcccaccaa atatggcaag  1260
tactggtgtt ggtgcttttg gtcactcgag gttgaggtgt tagacttgct cagtgctaaa  1320
gaaattgctg ttcgagcttg ggatgagacc ctcaatactc aacccgagaa gcttatttgg  1380
aacgtcatgg gaatgatgaa taattgctgg ttccgagtaa agatgaatgt gtgcaagcct  1440
cacaagggag agattggaat agtgtttgag catccgactc aacctggaaa ccaatcaggt  1500
ggatggatgg cgaaggagag acatttggag atatcagcag aggcacctca aacactaaag  1560
aagagtatcg atactccatt catgaacaca gcttccaaga tgtactccat gtccgaggtc  1620
aggaaacaca gctctgctga ctctgcttgg atcatagtcc atggtcatat ctatgacgcc  1680
acgcgtttct tgaaagatca ccctggtggg actgacagca ttctcatcaa tgctggcact  1740
gattgcactg aggaatttga tgcaattcat tctgataagg ctaagaagct cttggaggat  1800
ttcaggattg gtgaactcat aactactggt tacacctctg actctcctgg caactccgtg  1860
cacggatctt caagcttcag cagctttcta gcacctatta aggaacttgt tccagcgcag  1920
aggagtgtgg ccctaattcc aagagagaaa atcccatgca aactcatcga caagcaatcc  1980
atctcccatg atgttaggaa atttcgattt gcattgccct ctgaggatca agtcttgggc  2040
ttgcctgttg gaaaacatat cttcctctgt gccgttattg acgataagct ctgcatgcgc  2100
gcttacacgc ctactagcac gatcgatgag gtggggtact tcgagttggt tgtcaagata  2160
tacttcaaag gaattcaccc taaattcccc aatggagggc aaatgtcaca gtatcttgat  2220
```

-continued

```
tctatgccgt tagggtcatt tctcgacgtg aaaggtccat taggtcacat tgaataccaa  2280
ggaaagggaa atttcttagt tcatggcaaa cagaagtttg ccaagaagtt ggccatgata  2340
gcaggtggaa caggaataac tccagtgtat caagtcatgc aggcaattct gaaagatcca  2400
gaagatgaca cagaaatgta tgtggtgtat gctaacagaa cagaggatga tattttactt  2460
aaggaagagc ttgattcatg ggctgagaaa attccagaga gggttaaagt ttggtatgtg  2520
gttcaggatt ctattaaaga aggatggaag tacagcattg gttttattac agaagccatt  2580
ttgagagaac atatccctga gccatctcac acaacactgg ctttggcttg tggaccacct  2640
cctatgattc aatttgctgt taatccaaac ttggagaaga tgggctatga cattaaggat  2700
tccttattgg tgttctaagt cgac                                          2724

SEQ ID NO: 25          moltype = DNA  length = 2724
FEATURE                Location/Qualifiers
source                 1..2724
                       mol_type = other DNA
                       organism = Nicotiana tabacum
CDS                    4..2718
SEQUENCE: 25
catatggcgg catctgtcga aaacaggcag ttcagtcacc tagaagccgg tttatcccgg  60
tctttcaagc cccggtctga ttccccggtt cgtggctgca acttcccttc gcccaacagt  120
actaatttcc aaaagaaacc aaattccacc atttaccttg attactcgtc gagtgaagac  180
gacgatgatg atgacgaaaa aaatgagtac cttcaaatga ttaaaaaagg gaattcagag  240
ttagagccat ctgttcatga cactagggac gaaggtaccg ctgataattg gattgaacgc  300
aacttttcca tgattcgtct caccggaaag catccattta actccgaacc accgttgaac  360
cggctcatgc accacggctt tatcacaccg gtcccacttc attacgttcg taaccatgga  420
ccggttccca agggcacgtg ggatgactgg accgtggaag tcacgggact agtgaagcgt  480
cctatgaaat tcacaatgga ccagttggtt aacgaattcc cttgtagaga attgcccgtt  540
acgcttgttt gtgctggcaa tcgaaggaaa gaacagaaca tggttaaaca aaccattggt  600
ttcaactggg gcgccgctgc cgtttcaaca acgatatggc gcggggtacc cctccgcgct  660
ttgctaaaac ggtgcggtgt ttttagcaag aataaagggg cgcttaatgt ttgcttcgaa  720
ggagctgatg tgttgcccgg aggtggtggt tcaaagtatg gaaccagcat taagaaggaa  780
tttgcaatgg atccagcacg agatatcatc gtagcctaca tgcagaacgg agaaaaattg  840
gcacccgacc acgggtttcc agtacgaatg ataattccag gattcattgg aggaagaatg  900
gtgaaatgga taaagaggat tatagtcacc acccaagaat cagacagcta ttatcatttc  960
aaggacaata gagttcttcc tccccatgtt gatgctgaac ttgcaaatac cgaagcatgg  1020
tggtacaagc cagagtatat catcaatgag cttaatatta actctgtcat tacgacgccg  1080
tgtcatgaag aaattttgcc aattaacgcc tggacgactc agcgacctta cacgttgagg  1140
ggctattctt attctggcgg agggaaaaaa gtaacgcgag tagaagtgac gttggatgga  1200
ggagaaacat ggcaagttag cacactagat cacccagaga agcccaccaa atatggcaag  1260
tactggtgtt ggtgcttttg gtcactcgag gttgaggtgt tagacttgct cagtgctaaa  1320
gaaattgctg ttcgagcttg ggatgagacc ctcaatactc aacccgagaa gcttatttgg  1380
aacgtcatgg gaatgatgaa taattgctgg ttccgagtaa agatgaatgt gtgcaagcct  1440
cacaagggag agattggaat agtgtttgag catccgactc aacctggaaa ccaatcaggt  1500
ggatggatgg cgaaggagag acatttggag atatcagcag aggcacctca aacactaaag  1560
aagagtatct caactccatt catgaacaca gcttccaaga tgtactccat gtccgaggtc  1620
aggaaacaca gctctgctga ctctgcttgg atcatagtcc atggtcatat ctatgacgcc  1680
acgcgtttct tgaaagatca ccctggtggg actgacagca ttctcatcaa tgctggcact  1740
gattgcactg aggaatttga tgcaattcat tctgataagg ctaagaagct cttggaggat  1800
ttcaggattg gtgaactcat aactactggt tacacctctg actctcctgg caactccgtg  1860
cacggatctt caagcttcag cagctttcta gcacctatta aggaacttgt tccagcgcag  1920
aggagtgtgg ccctaattcc aagagagaaa atcccatgca aactcatcga caagcaatcc  1980
atctcccatg atgttaggaa atttcgattt gcattgccct ctgaggatca agtcttgggc  2040
ttgcctgttg gaaaacatat cttcctctgt gccgttattg acgataagct ctgcatgcgc  2100
gcttacacgc ctactagcac gatcgatgag gtggggtact tcgagttggt tgtcaagata  2160
tacttcaaag gaattcaccc taaattcccc aatggagggc aaatgtcaca gtatcttgat  2220
tctatgccgt tagggtcatt tctcgacgtg aaaggtccat taggtcacat tgaataccaa  2280
ggaaagggaa atttcttagt tcatggcaaa cagaagtttg ccaagaagtt ggccatgata  2340
gcaggtggaa caggaataac tccagtgtat caagtcatgc aggcaattct gaaagatcca  2400
gaagatgaca cagaaatgta tgtggtgtat gctaacagaa cagaggatga tattttactt  2460
aaggaagagc ttgattcatg ggctgagaaa attccagaga gggttaaagt ttggtatgtg  2520
gttcaggatt ctattaaaga aggatggaag tacagcattg gttttattac agaagccatt  2580
ttgagagaac atatccctga gccatctcac acaacactgg ctttggcttg tggaccacct  2640
cctatgattc aatttgctgt taatccaaac ttggagaaga tgggctatga cattaaggat  2700
tccttattgg tgttctaagt cgac                                          2724
```